United States Patent [19]

Li et al.

[11] Patent Number: 5,133,723
[45] Date of Patent: Jul. 28, 1992

[54] SUTURE RUNDOWN TOOL AND CUTTER SYSTEM

[75] Inventors: Lehmann K. Li, Wellesley; John T. Rice, Lincoln, both of Mass.

[73] Assignee: Mitek Surgical Products, Inc., Norwood, Mass.

[21] Appl. No.: 725,195

[22] Filed: Jul. 3, 1991

Related U.S. Application Data

[63] Continuation-in-part of Ser. No. 544,409, Jun. 27, 1990, Pat. No. 5,084,058, which is a continuation-in-part of Ser. No. 514,179, Apr. 25, 1990, Pat. No. 5,087,263.

[51] Int. Cl.[5] .............................................. A61B 17/00
[52] U.S. Cl. .................................. 606/148; 606/139; 289/17
[58] Field of Search ................ 606/148, 139, 144–147; 289/1.5, 2, 17

[56] References Cited

U.S. PATENT DOCUMENTS

| | | | |
|---|---|---|---|
| 2,595,086 | 4/1952 | Larzelere | 606/139 |
| 3,856,018 | 12/1974 | Perisse et al. | 606/139 |
| 4,602,635 | 7/1986 | Mulhollan et al. | |
| 4,961,741 | 10/1990 | Hayhurst | 606/139 |

FOREIGN PATENT DOCUMENTS 1169630  7/1985  U.S.S.R. ............................. 606/139

*Primary Examiner*—Stephen C. Pellegrino
*Assistant Examiner*—Gary Jackson
*Attorney, Agent, or Firm*—Pandiscio & Pandiscio

[57] ABSTRACT

A suture throw holder, rundown tool and cutting system for running one or more throws formed in two lengths of suture extending from a surgical site down to the surgical site so as to form a knot at the surgical site and for blindly cutting the suture ends adjacent the knot. The system comprises a support mechanism for releasably supporting a plurality of throws in a predetermined arrangement adjacent a surgical site, and a tool for removing throws from the support mechanism, running the throws down the lengths of the suture to the surgical site, and blindly cutting the suture ends at substantially equal lengths every time adjacent a knot formed by the throws at the surgical site.

18 Claims, 25 Drawing Sheets

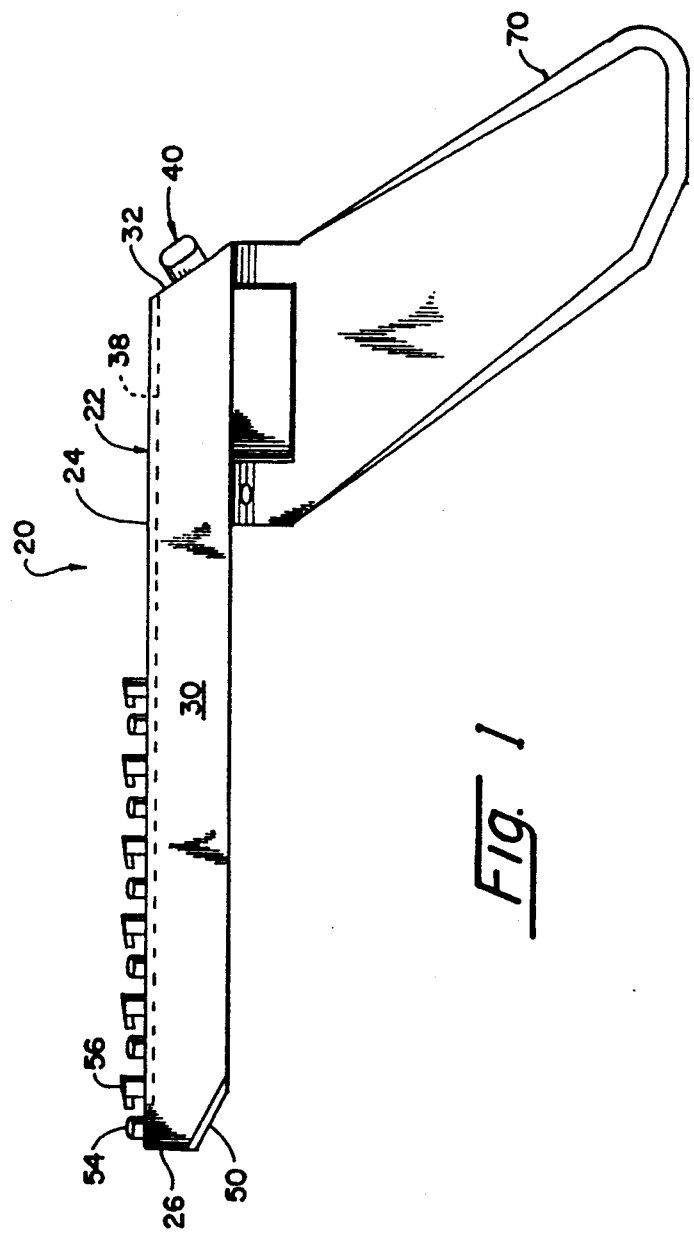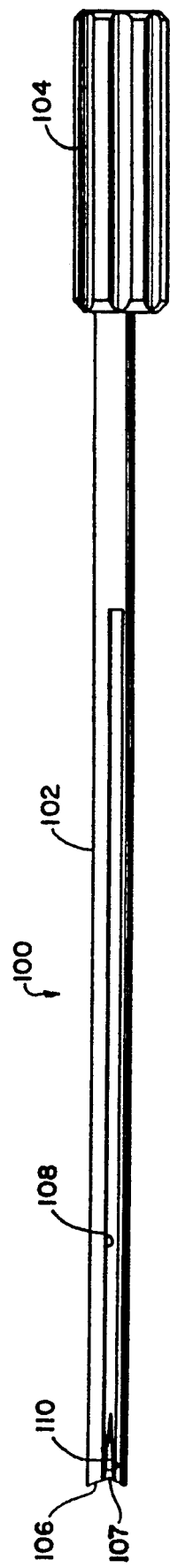

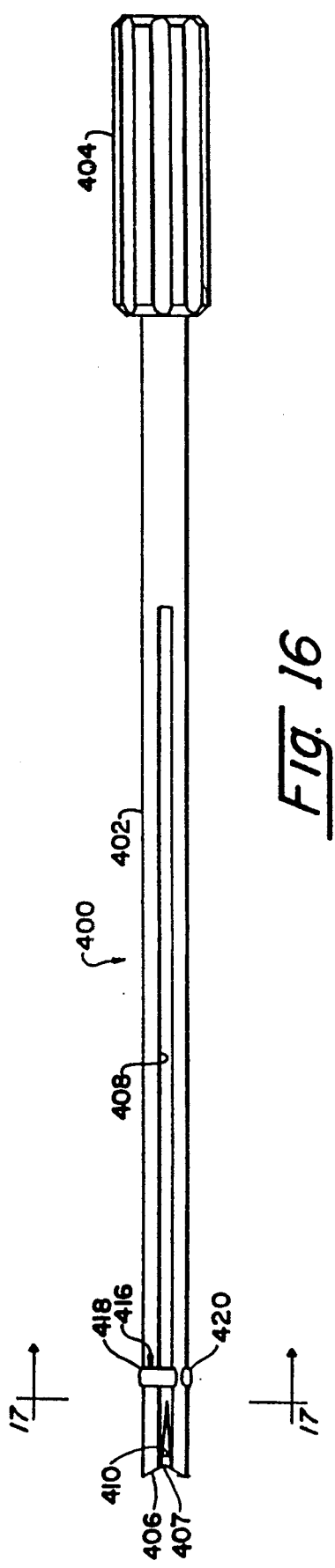
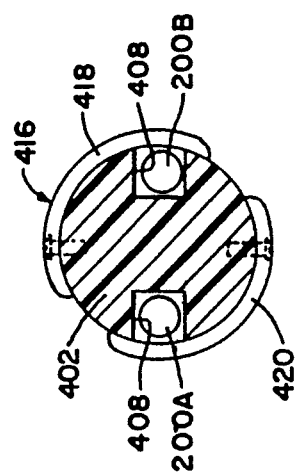
Fig. 16
Fig. 17

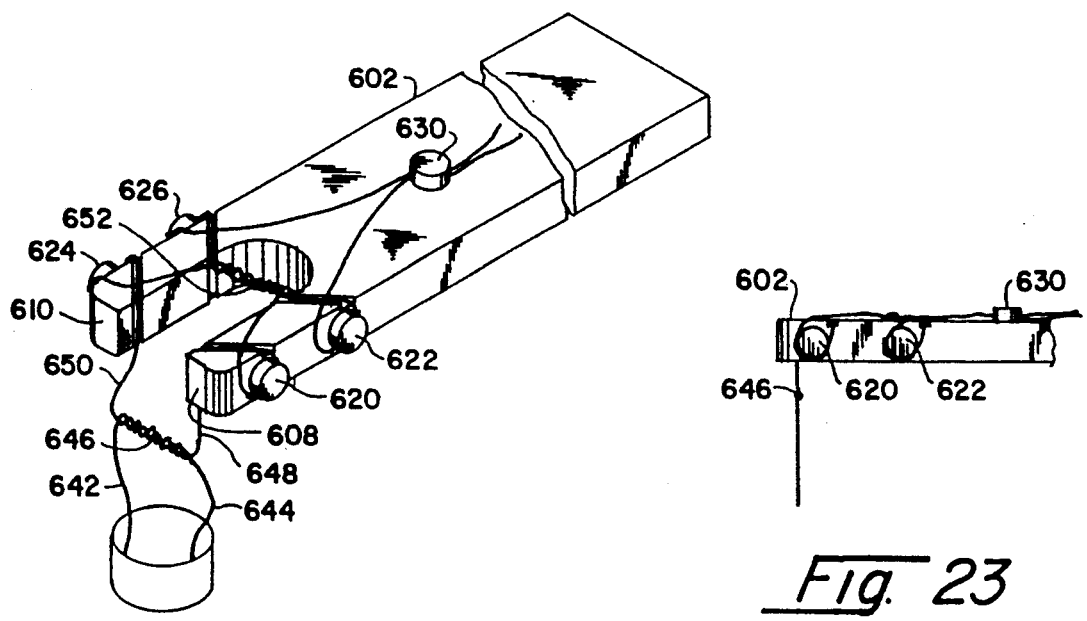
Fig. 22
Fig. 23
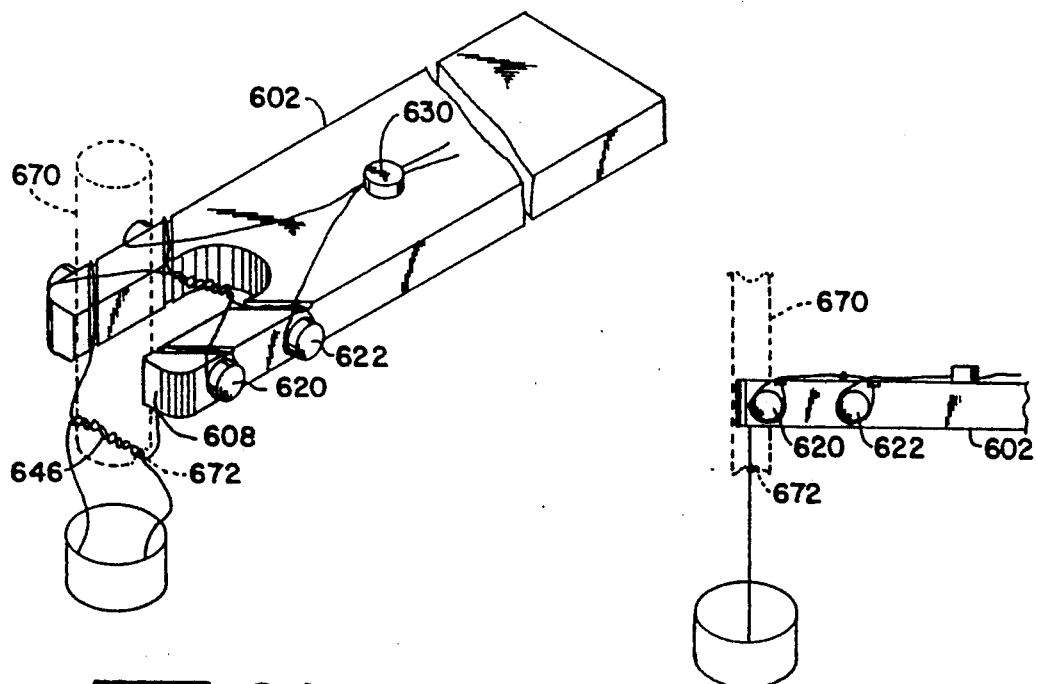
Fig. 24
Fig. 25

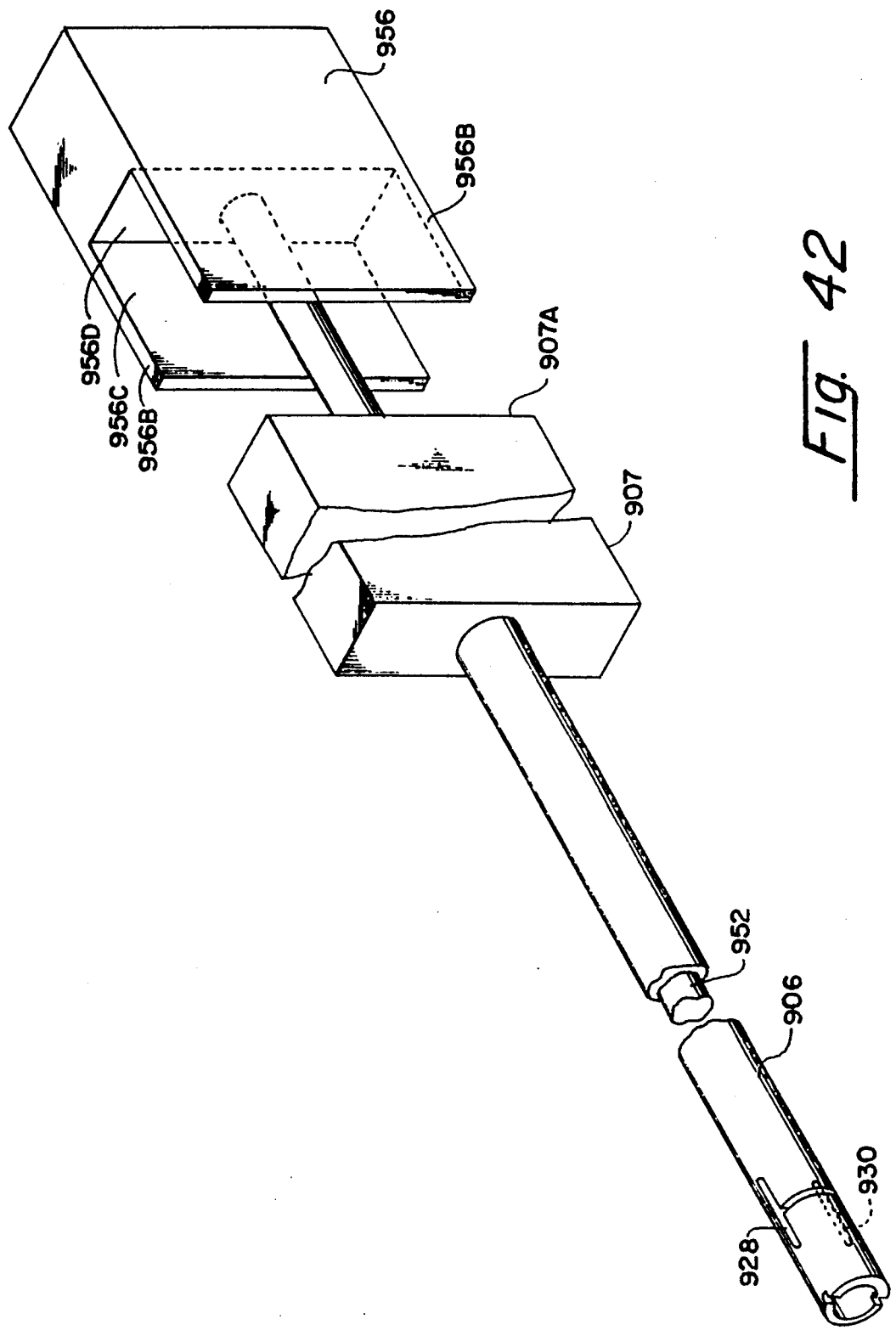

SUTURE RUNDOWN TOOL AND CUTTER SYSTEM

CROSS-REFERENCE TO RELATED APPLICATIONS

This is a continuation-in-part of application Ser. No. 07/544,409; filed Jun. 27, 1990, now U.S. Pat. No. 5,084,058, entitled Suture Rundown Tool and Cutter System, which was in turn a continuation-in-part application of Ser. No. 07/514,179; filed Apr. 25, 1990, now U.S. Pat. No. 5,087,263, for Suture Throw Holder and Rundown System.

BACKGROUND OF THE INVENTION

1. Field of the Invention

The present invention relates to surgical instruments for securing sutures in tissue and, more particularly, is directed to instruments for forming a plurality of suture throws at a location remote from a surgical site, running the throws serially down the lengths of suture so as to form a knot at the surgical site, and cutting the suture ends adjacent the knot.

2. Description of the Prior Art

In both closed (e.g. arthroscopic) and open surgeries, it is frequently necessary to form a knot at a surgical site using two lengths of suture emanating from the surgical site, wherein the two lengths of suture must be manipulated with respect to one another at a location remote from the surgical site.

With one known procedure, a "taut-line hitch" knot is formed in the loose ends of the suture at a location remote from the surgical site from which the suture ends emanate, and then the knot is run down the suture ends to the surgical site by pulling with a sawing motion on the appropriate suture ends. A significant drawback to this procedure is that as the appropriate suture end is pulled through the tissue in which the suture is implanted so as to run the knot down to the surgical site, the sawing motion imparted to the suture ends causes the latter to tend to cut and abrade the tissue.

An alternative procedure consists of forming a throw in the suture at a location remote from the surgical site from which the suture ends emanate, running the throw down the length of suture to the surgical site, forming a second throw in the suture at a location remote from the surgical site, running that throw down the length of suture to the surgical site so that it sits atop the first throw, and thereafter repeating the foregoing process as many times as necessary so as to form the desired knot at the surgical site. As used herein, a "turn" consists of two ends of suture which are looped over one another one or more times, a "throw" consists of one or more turns, and a "knot" consists of two or more throws laid on top of one another and tightened so as to lock the two strands of suture relative to one another. Once the knot has been made, the free suture ends are cut near the knot by means of surgical scissors or the like.

In cases of open surgical procedures, such as abdominal surgery, the trimming of free suture ends in this manner (or with a knife) presents little problem. In the case of so-called closed surgical procedures, such as arthroscopic procedures, however, the trimming of free suture ends is more problematic. Conventional scissors or knife blades are unable to reach the surgical site because of the small nature of the incisions involved. Consequently, the use of such trimming mechanisms is inappropriate. Long free suture ends after trimming are almost always undesirable, and may be damaging in closed and/or microscopic surgical cases. Miniaturized surgical scissors and knives exist which may extend through small incisions to a closed surgical site, but the insertion, removal and positioning of these devices are sometimes difficult, and are not without risk. For example, it will be understood that once the suture knot is set, the trimming operation requires the removal of the rundown tool and the subsequent insertion of the cutting tool. This sequence not only adds steps to an already delicate procedure, but also introduces risks of tool and tissue damage. Specifically, the tool may damage the walls of the incision or itself be nicked or dulled during insertion through a cannula to the surgical site. Also, once present at the surgical site, the tool must be manipulated to contact and sever the free suture ends. The latter manipulation is inherently dangerous, and may adversely impact upon the success of the entire surgical procedure. Additionally, the presence of unguarded knife edges in the operating theater always presents risk to operating room personnel as well as patients. The provision of guarding mechanisms for cutting edges accordingly is desirable where such is possible without adverse impact upon the surgical procedure or technique involved.

Arthrex Arthroscopy Instruments, Inc. of Black Rock, Conn. manufactures several tools for running a suture throw down suture ends to a surgical site from a location remote from the surgical site. One such tool is identified as the Arthrex Arthroscopy Knot Pusher (Model No. AR-1310). This knot pusher comprises an elongate shaft having an end portion which is inclined slightly with respect to the long axis of the shaft. The end portion includes a bore extending therethrough. After a throw is formed in the suture ends at a location remote from the surgical site from which the suture ends emanate, one of the ends is threaded through the bore in the end portion of the knot pusher. Then the tool is run down the length of that suture end, while maintaining appropriate tension on the suture ends, so as to push the throw toward the surgical site. Once the first throw has been run down the suture lengths to the surgical site, another throw may be formed in the suture ends at a location remote from the surgical site and then run down the suture ends to the surgical site so that it sits atop the first throw. This procedure may be repeated as many times as desired so as to form a knot at the surgical site.

Arthrex Arthroscopy Instruments, Inc. manufactures another knot pusher tool identified as Model No. AR-1311. This tool comprises an elongate shaft having a rounded front end, and a pair of holes extending in from the sides of the shaft at an angle and terminating at the front end of the shaft. To use the Model No. AR-1311 tool, a throw is formed in the suture ends emanating from the surgical site. Then, each of the free ends of the suture extending away from the throw is threaded into a corresponding respective one of the holes in the front end of the tool and caused to pass out the end of that hole intersecting the side of the tool. Next, the surgeon grasps the suture ends extending out of the holes in the sides of the tool and applies tension to the suture ends. Thereafter, while maintaining this tensioning of the suture ends, the surgeon urges the tool toward the surgical site by pushing against the rear end of the tool, typically with his or her stomach, thereby causing the tool to run the throw down the suture ends to the surgical site. As the throw is run down to the surgical site, successive portions of the suture ends emanating from the surgical site pass through the holes in the rundown tool. Finally, the rundown tool is extracted from the surgical site, whereby the suture ends pass back through, and ultimately are removed from the holes in the rundown tool. Subsequent throws are run down to the surgical site following this procedure.

Yet another Arthrex rundown tool is illustrated, although not described, on page 7 of a brochure published by Arthrex Arthroscopy Instruments, Inc. entitled "The Arthrex Grasping Stitcher System". This rundown tool comprises an elongate shaft which apparently has a rounded or convex V-shaped front end, and a pair of axially-extending, diametrically opposed grooves which terminate at the front end of the tool. A ring surrounds and engages the front end of the shaft, whereby the grooves are surrounded by the ring. This Arthrex tool apparently functions substantially identically to the Arthrex tool Model No. AR-1310 described above, except that each of the suture ends is positioned in a respective one of the elongate grooves and is passed underneath the surrounding ring, rather than being threaded in the holes at the front end of the Arthrex tool Model No. AR-1310.

The operation of all three of the above-mentioned rundown tools of the Arthrex Arthroscopy Instruments, Inc., contemplates that the free ends of the suture after the knot is set are to be trimmed in one of the well known manners discussed above.

SUMMARY OF THE INVENTION

An object of the present invention is to provide a suture throw holder rundown tool and cutter system in which the throw holder and rundown system permits a plurality of throws, formed in two lengths of suture emanating from a surgical site, to be prelaced and held in a location remote from the surgical site, and then to be quickly and easily run down the suture ends to the surgical site so as to form a knot at the surgical site, and in which the cutter permits the suture ends to be blindly cut to substantially the same length every time adjacent the knot.

Another object of the present invention is to provide a suture holder, rundown tool and cutter system in which the suture throw holder and rundown system permits a plurality of throws to be tied in suture ends which extend away from a surgical site and to be supported in a location remote from the surgical site, whereby the throws can be run down the suture ends one after another to the surgical site without the need to pause and tie a new throw after a preceding throw is run down the suture ends to the surgical site and the cutter is guided in a bore formed in the suture rundown system to blindly cut the suture ends to substantially the same length every time adjacent the knot.

Yet another object of the present invention is to provide a suture throw holder rundown tool with a cutter which permits a multiple-turn throw to be run down the suture ends extending from a surgical site to form a knot and permits the suture ends to be blindly cut to substantially the same length every time adjacent the knot.

Still another object of the present invention is to provide a suture throw holder, rundown tool and cutter system which automatically maintains substantially equal tension on the suture ends emanating from a surgical site while throws are being run down the suture ends to the surgical site and permits the suture ends to be blindly cut to substantially the same length every time adjacent the knot without injury to adjacent tissue.

These and other objects are achieved by a suture throw holder, rundown tool and cutter system comprising (1) a support mechanism for releasably supporting, adjacent a surgical site, a plurality of suture throws formed from suture ends extending from the surgical site, (2) a rundown tool for removing the throws from the support mechanism and for running the throws down the suture ends to the surgical site to form a knot and (3) a cutter for blindly cutting the suture ends to substantially same length every time adjacent the knot.

The support mechanism comprises a top surface to which a plurality of groups of four pegs are attached. The pegs are arranged so as to permit (a) the lengths of suture extending from the surgical site to be interwoven between the pegs, and (b) throws formed using the interwoven portions of the suture to be releasably supported adjacent each of the groups of pegs so as to extend away from the leading edge of the support mechanism in a linear array. Each group of four pegs consists of two subgroups of two pegs each, two leading and two trailing; the suture ends are woven around the outside of the first subgroup of two pegs and around the inside of the second subgroup of two pegs, with the throws being captivated about the two subgroups of pegs. The support mechanism also includes two pairs of legs for supporting the top surface in a predetermined orientation relative to the surgical site.

The suture throw rundown tool comprises an elongate shaft including means in the front end thereof for engaging the respective throws as they are run down the suture ends. In the various embodiments of the invention to be discussed in detail below, this means may comprise a groove extending transversely across the front end face of the rundown tool; a depression of the central portion of the front end face of the rundown tool connected on opposite sides of the front face to the outer surface of the shaft by grooves; or grooves on opposite front end walls of a hollow shaft. The shaft also may include a pair of diametrically opposed elongate grooves formed in the side walls of the shaft which intersect and extend rearwardly from the front end of the shaft along a portion of the axis of the shaft to form an internal cavity. In this embodiment, a transverse slot intersects the grooves and communicates with the cavity. The slot and grooves are sized to receive the suture. The shaft is formed with a central bore that extends at least substantially the entire length of the tool. In the embodiment just mentioned, this bore intersects the cavity formed by the grooves. In another embodiment, the bore extends the entire length of the tool, and the elongated grooves are replaced by diametrically opposed longitudinal slots spaced slightly proximally from the front end of the tool in alignment with the grooves in the front end wall.

The cutter comprises an elongate shaft having cutting means at its front end and a handle at its back end. The cutter shaft is sized and shaped to be slidably received in the central bore formed in the tool shaft such that the central bore defines a guideway for the cutter shaft.

The cutting means comprises at least one cutting blade flanked adjacent the outer periphery of the forward end of the shaft by proximally extending shoulders such that the blade(s) are protected from inadvertent damage, and users of the device are protected from inadvertent injury. Suture end trimming is not adversely impacted because the suture strands held in the rundown tool easily fit between the shoulders for engagement with and severing by the blade(s).

In a preferred embodiment, both the rundown tool and the cutter include handle members adjacent to their proximal ends. The axial geometric cross-section of these handle members correspond to each other such that when the forward end of the cutter handle is brought in contact with the rear end of the rundown tool handle the user may be assured that the cutting blade(s) are correctly oriented for suture trimming when the handle cross-sections are aligned.

In use, a first throw is formed on the support mechanism using the two ends of suture extending from the surgical site. The first throw is releasably secured to the group of pegs closest to the front end of the support mechanism. Subsequent throws are formed using the remaining portions of the suture ends and are releasably secured to corresponding respective groups of pegs. Then, the lengths of suture leading from the surgical site to the first throw are detached from the two leading pegs of the first group around which they are wrapped by appropriately manipulating the support mechanism. Next, the first throw is engaged by the throw rundown tool by inserting the throw in the throw engagement means in the front of the shaft of the rundown tool. Then the shaft, with throw captivated thereagainst, is urged toward the surgical site, pushing the throw down the suture ends ahead of the rundown tool, until the throw is positioned adjacent the tissue surface from which the lengths of suture emanate. Subsequent throws are run down to the surgical site in the sequence they are supported on the support mechanism following the foregoing procedure, whereby a knot is formed in the suture at the surgical site. Thereafter, the cutter is urged downwardly in the central bore and the cutter blade severs the suture ends substantially equally adjacent the knot.

Still other objects and features of the invention will in part be obvious and will in part appear hereinafter. The invention accordingly comprises the apparatus possessing the construction, combination of elements, and arrangement of parts which are exemplified in the following detailed disclosure. The scope of the present invention will be indicated in the claims.

BRIEF DESCRIPTION OF THE DRAWINGS

For a fuller understanding of the nature and objects of the present invention, reference should be made to the following detailed description taken in connection with the accompanying drawings wherein:

FIG. 1 is a side elevation view of the suture throw support device;

FIG. 2 is a plan view of the throw rundown tool showing a V-shaped groove in the front of the tool in profile;

FIG. 16 is a plan view of an alternative embodiment of the throw rundown tool showing a V-shaped groove in the front of the tool in profile;

FIG. 17 is an enlarged cross-sectional view taken along line 17—17 in FIG. 16;

FIG. 22 is similar to FIG. 20, except that the suture portions extending away from the surgeon's knot have been wrapped around the front pegs of the holder, formed into a single-turn throw, wrapped around the rear pegs of the holder, and anchored to the clamp of the holder;

FIG. 23 is a side elevation view of the holder and suture ends shown in FIG. 22;

FIG. 24 is similar to FIG. 22 except that a knot rundown tool has been moved into engagement with the surgeon's knot supported adjacent the holder;

FIG. 25 is a side elevation view of the holder, rundown tool, and suture ends shown in FIG. 24;

FIG. 42 is a perspective view in side elevation of another rundown tool and cutter system embodying the present invention which utilizes an alternative handle configuration to assure the desired alignment of the rundown tool with the cutter during the suture severing operation.

DETAILED DESCRIPTION OF THE PREFERRED EMBODIMENTS

Figure 3:
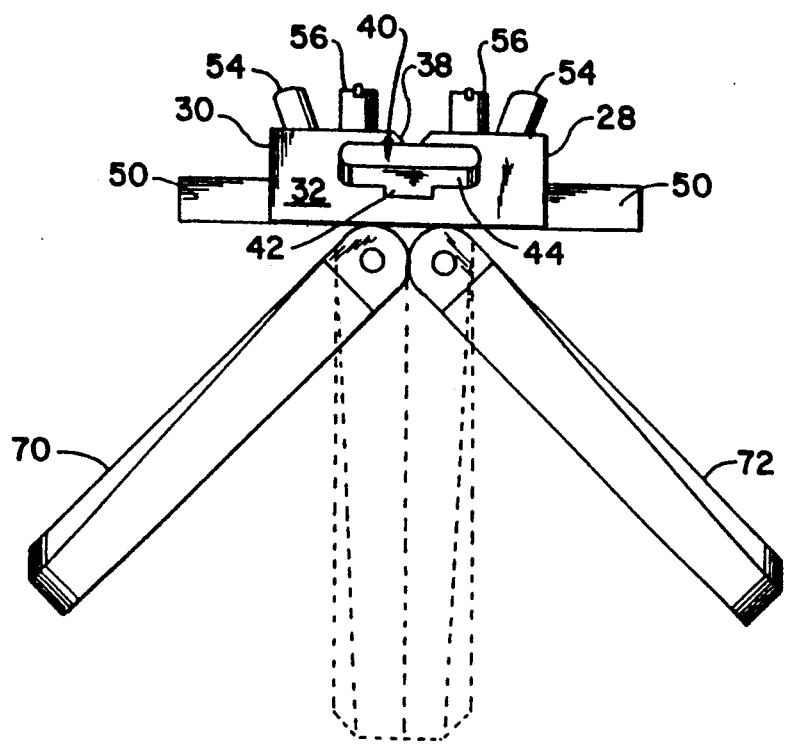
FIG. 3 is a rear elevation view of the suture throw support device, with the legs of the device being shown in the open position in solid view and in the closed position in phantom view.

Referring first to FIGS. 1-4, there is shown is a suture throw holder and rundown system for releasably supporting a plurality of suture throws formed using two loose ends of suture extending away from a surgical site and for successively running the throws down the lengths of suture to the surgical site so as to form a knot in the suture ends adjacent the surface of the tissue at the surgical site. The suture throw holder and rundown system of the present invention comprises a suture throw support device 20 and a rundown tool 100.

Support device 20 comprises an elongate frame 22 having a top surface 24, a front surface 26, side surfaces 28 and 30 (FIGS. 1, 3 and 4), and a rear surface 32. The length of top surface 24 (as measured between front surface 26 and rear surface 32) is preferably significantly greater than its width (as measured between side surfaces 28 and 30). In an exemplary embodiment of the present invention, top surface 24 measures about 6" long and 2" wide.

Frame 22 includes an elongate groove 38 (FIGS. 1, 3 and 4) formed in top surface 24. Groove 38 is positioned so that its long axis extends parallel to the long axis of top surface 24 and so that it bisects the width of the top surface. Groove 38 is sized to receive a front portion of throw rundown tool 100, as discussed hereinafter.

Figure 4:
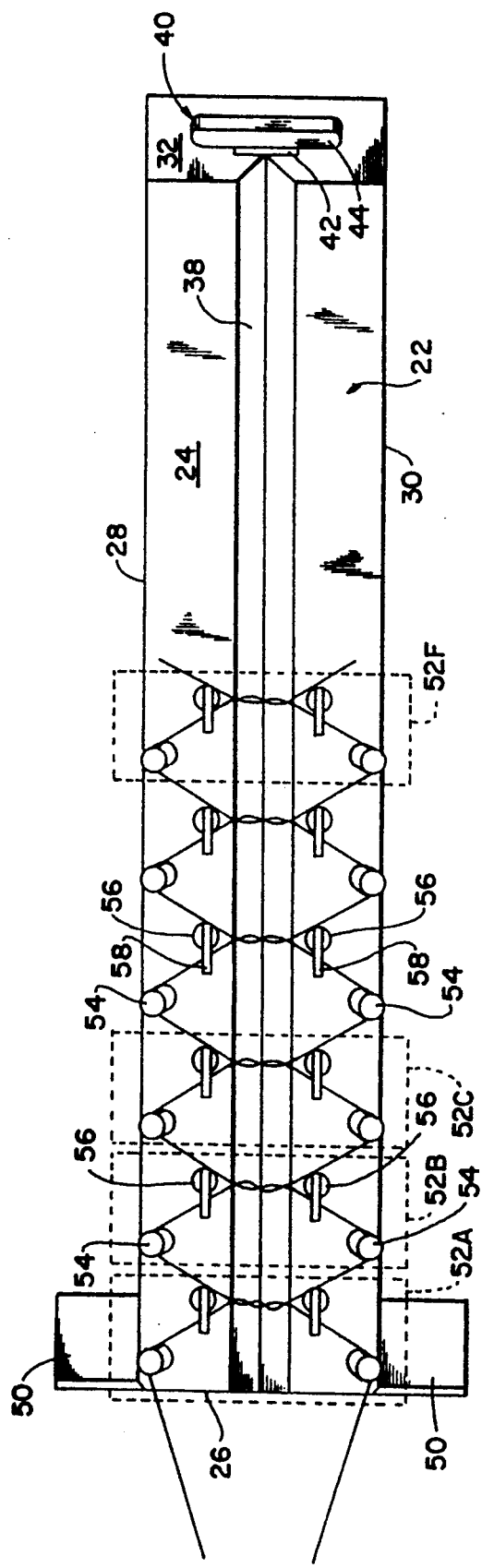
FIG. 4 is a plan view of the suture throw support device, with suture attached.

Frame 22 also includes a cleat 40 attached to rear surface 32 (FIGS. 1, 3 and 4). Cleat 40 includes a base 42 attached to rear surface 32, and an elongate member 44 attached to base 42. Base 42 is sized so that the elongate member 44 is elevated slightly above rear surface 32, thereby permitting lengths of suture to be wedged between rear surface 32 and the bottom of elongate member 44, as discussed hereinafter.

Frame 22 additionally comprises a pair of feet 50 (FIGS. 1, 3 and 4) attached to the front end of the frame adjacent its front surface 26. Feet 50 project out from the side surfaces 28 and 30 of the frame, and the bottom surfaces of the feet are inclined at about a 45° angle relative to front surface 26, as seen in FIG. 1.

Frame 22 further includes a plurality of groups 52 (FIG. 4) of pegs for releasably supporting suture throws on the frame. Each group 52 comprises a pair of leading pegs 54 and a pair of trailing pegs 56. Pegs 54 and 56 have a solid, elongate, preferably cylindrical configuration, although pegs of other cross-sectional configurations may also be employed. In an exemplary embodiment, pegs 54 and 56 extend about 0.5" above the plane of surface 24. Each of the trailing pegs 56 includes an elongate finger 58, one end of which is attached to the top surface of each of the trailing pegs so as to extend toward front surface 26.

Pegs 54 are attached to top surface 24 so that they pitch outwardly and forwardly slightly, toward side surfaces 28 and 30, in the manner shown in FIG. 3. Pegs 56 are attached to top surface 24 so as to extend substantially perpendicular thereto, in the manner shown in FIG. 3. Additionally, pegs 54 lie along a leading plane which extends perpendicular to both top surface 24 and the long axis of the top surface, and pegs 56 lie along a trailing plane which extends perpendicular to both top surface 24 and the long axis of the top surface, with the leading plane (i.e., the plane of leading pegs 54) being positioned closer to front surface 26 than the trailing plane (i.e., the plane of trailing pegs 56). Leading pegs 54 are positioned adjacent side surfaces 28 and 30, while trailing pegs 56 are positioned inboard from the side surfaces, adjacent groove 38 (see FIGS. 3 and 4). In an exemplary embodiment of the present invention, leading pegs 54 are spaced apart about 1.75", trailing pegs 56 are spaced apart about 1", and the leading plane on which pegs 54 lie is spaced about 0.25" closer to front surface 26 than the corresponding trailing plane on which pegs 56 lie.

Support device 20 additionally comprises a pair of legs 70 and 72 (FIGS. 1 and 3) which are attached to the bottom of frame 22 adjacent its rear surface 32. Legs 70 and 72 are pivotally mounted to frame 22 so as to be movable between an open position (shown in solid view in FIG. 3) and a closed position (shown in phantom view in FIG. 3). In the open position legs 70 and 72 extend outboard of side surfaces 28 and 30 in an inverted V-shaped configuration, while in the closed position legs 70 and 72 are positioned inboard of side surfaces 28 and 30 in a parallel, pistol-grip configuration. A detent stop mechanism (not shown) is provided for releasably securing legs 70 and 72 in an open position (shown in FIG. 3). Legs 70 and 72 are sized and configured so that the user of suture throw support device 20 can grasp the legs in his or her hands when the legs 70 and 72 are positioned in their closed position, as discussed hereinafter. Additionally, legs 70 and 72 are sized and configured so that when the support device 20 is positioned so that its front feet 50 and its rear legs 70 and 72 rest on a surface adjacent a surgical site, with legs 70 and 72 in the open position, the support device will be maintained in a predetermined orientation relative to the surgical site, as discussed hereinafter.

Referring next to FIG. 2, knot rundown tool 100 comprises an elongate shaft 102 and a handle 104 attached to the rear end of the shaft. A convex, V-shaped groove 106 is provided in the front end of the shaft. The base (i.e., bottom) 107 of groove 106 intersects the longitudinal axis of shaft 102. Shaft 102 also includes a pair of diametrically-opposed elongate grooves 108, only one of which is shown in FIG. 1. The elongate grooves 108 intersect the base 107 of V-shaped groove 106 and extend rearwardly from the latter, parallel to the axis of the shaft. Shaft 102 additionally comprises a pair of diametrically-opposed, V-shaped notches 110, only one of which is shown in FIG. 1. Notches 110 are formed in the front ends of elongate grooves 108 so that the wide end of the notches intersects the base of V-shaped notch 106.

Operation of the suture throw holder and rundown system of the present invention will now be described.

Figure 5:
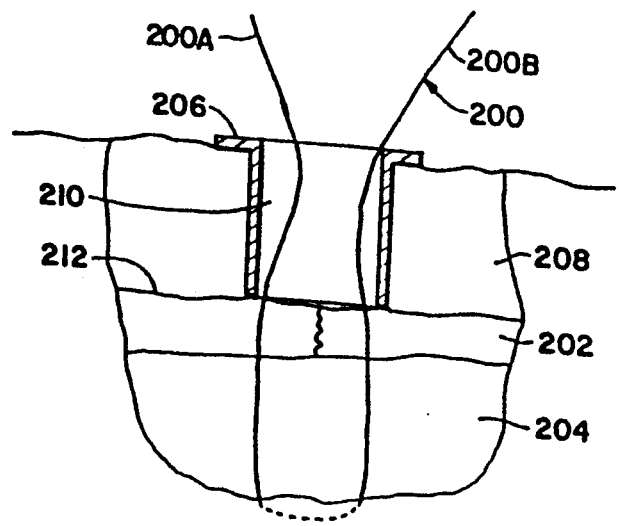
FIG. 5 is a side elevation view, partially in section, showing a suture deployed in a typical surgical site.

Looking next at FIG. 5, there is shown a representative surgical scenario in which the present invention might be used to maintain a plurality of suture throws, formed in two lengths of suture emanating from an interior surgical site, at a location remote from the surgical site, and to run them serially down the lengths of suture so as to form a knot at the surgical site. More specifically, in the representative surgical scenario depicted in FIG. 5, it might be desired to use a suture 200 to fasten an upper tissue piece 202 to a lower tissue piece 204, where the tissue pieces 202 and 204 are positioned deep within a bodily member, access being gained to the site via a hollow cannula 206 positioned in surface tissue 208.

In such a circumstance, the suture 200 would first be emplaced in tissue pieces 202 and 204 using methods well known in the art, so that an intermediate portion of the suture is positioned at the surgical site as needed, and the two suture ends 200A and 200B extend out through the hollow cannula's interior passageway 210 so that they reside outside the body. The present invention provides a means for supporting a plurality of throws formed using loose suture ends 200A and 200B adjacent the mouth of cannula 206, at a position outside the body, and for running the throws serially down the suture ends to the top surface 212 of upper tissue piece 202, whereby a knot may be formed at top surface 212 so as to effect the desired attachment of tissue pieces 202 and 204 to one another.

It should of course, be appreciated that the surgical scenario depicted in FIG. 5 (and discussed in the following description of the operation of the present invention) is merely one of many different surgical scenarios in which the present invention could be utilized, and is provided solely by way of illustration and not of limitation. As will be recognized by persons skilled in the art, the present invention could be used in a wide variety of other surgical scenarios in which it is desired to maintain a plurality of suture throws, formed in two lengths of suture emanating from an interior surgical site, at a location remote from the surgical site, and to run them serially down the length of suture so as to form a knot at the surgical site.

Figure 6:
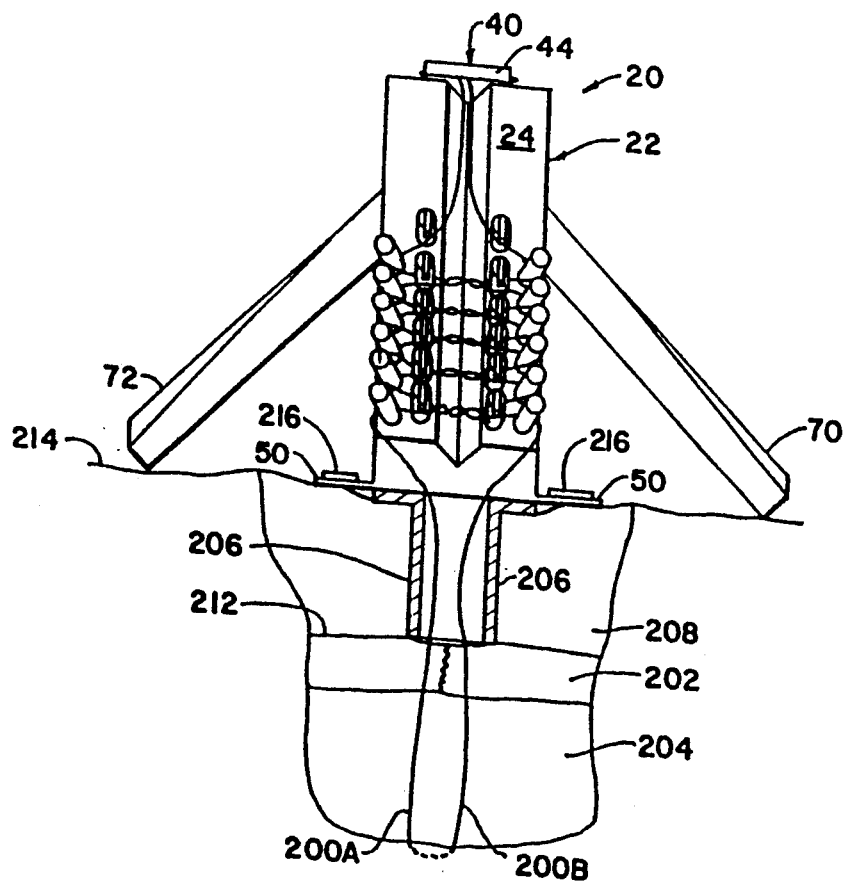
FIG. 6 is a front elevation view showing the suture throw support device resting on the surface of tissue adjacent a surgical site, which is shown in cross section.

Starting then with the surgical scenario depicted in FIG. 5, as a first step of using the present invention, legs 70 and 72 of support device 20 are spread apart to the open position, as illustrated in FIGS. 3 and 6. Then, support device 20 is positioned so that its feet 50 rest on surface 214 of surface tissue 208 adjacent cannula 206 and its legs 70 and 72 rest on surface 214 near cannula 206. Preferably, feet 50 are then secured to surface 214 using surgical tape 216 (FIG. 6). Feet 50 and legs 70 and 72 are sized and configured so that when support device 20 rests on tissue surface 214, top surface 24 of the frame 22 is inclined at about a 45° angle relative to skin top surface 214.

Figure 7:
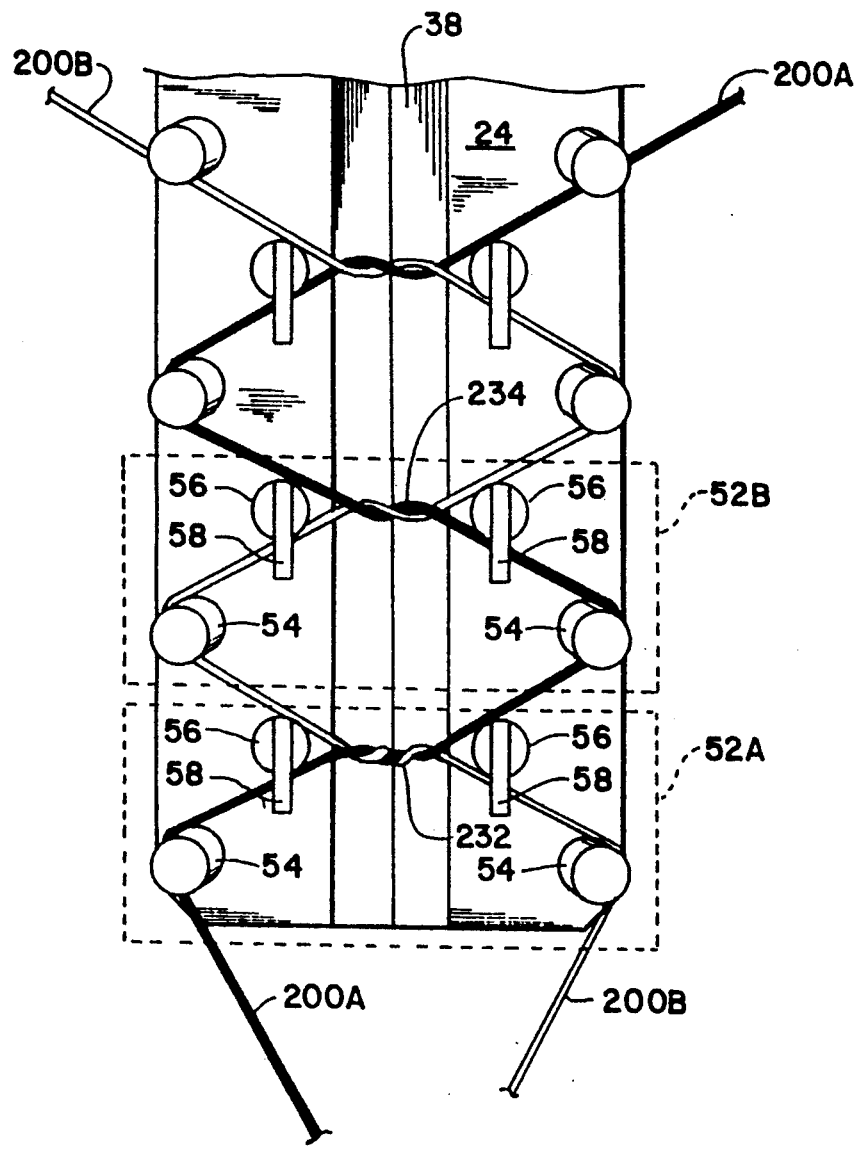
FIG. 7 is an enlarged plan view of the front portion of the suture throw support device shown in FIG. 4.

Next, a plurality of throws (formed using loose suture ends 200A and 200B) are releasably secured to pegs 54 and 56 of support device 20. To begin this process, suture ends 200A and 200B are wrapped around the outer surfaces of leading pegs 54 (FIG. 7) of the first group 52A of pegs and are positioned under fingers 58 of trailing pegs 56. Then, a first throw 232, preferably a double turn throw, is formed using those portions of ends 200A and 200B extending away from the pegs 54 (around which they are wrapped) toward rear surface 32 of support device 20.

Then, the portions of suture ends 200A and 200B extending from first throw 232 toward the second group 52B of pegs are wrapped around the inner surface of trailing pegs 56 of first group 52A, and are then wrapped around the outer surface of leading pegs 54 of second group 52B.

In the unusual event that only one throw is to be supported on frame 22, the portions of suture ends 200A and 200B leading rearwardly away from first throw 232 and around pegs 54 of second group 52B are tensioned and secured to cleat 40 by wrapping the suture ends around cleat base 42 and wedging the portions between rear surface 32 and the bottom surface of elongate member 44.

In the alternative (and more usual) event that multiple throws are to be supported on frame 22, the portions of suture ends 200A and 200B extending rearwardly from leading pegs 54 of group 52B are positioned under fingers 58 of trailing pegs 56 of group 52B, and a second throw 234 is formed using these portions of the suture ends. Additional throws are similarly formed as desired using suture ends 200A and 200B adjacent successive ones of peg groups 52. After the last throw is formed, the suture ends extending rearwardly from the last throw are tensioned and are secured to cleat 40, as discussed above, in the manner shown in FIG. 6.

Figure 8:
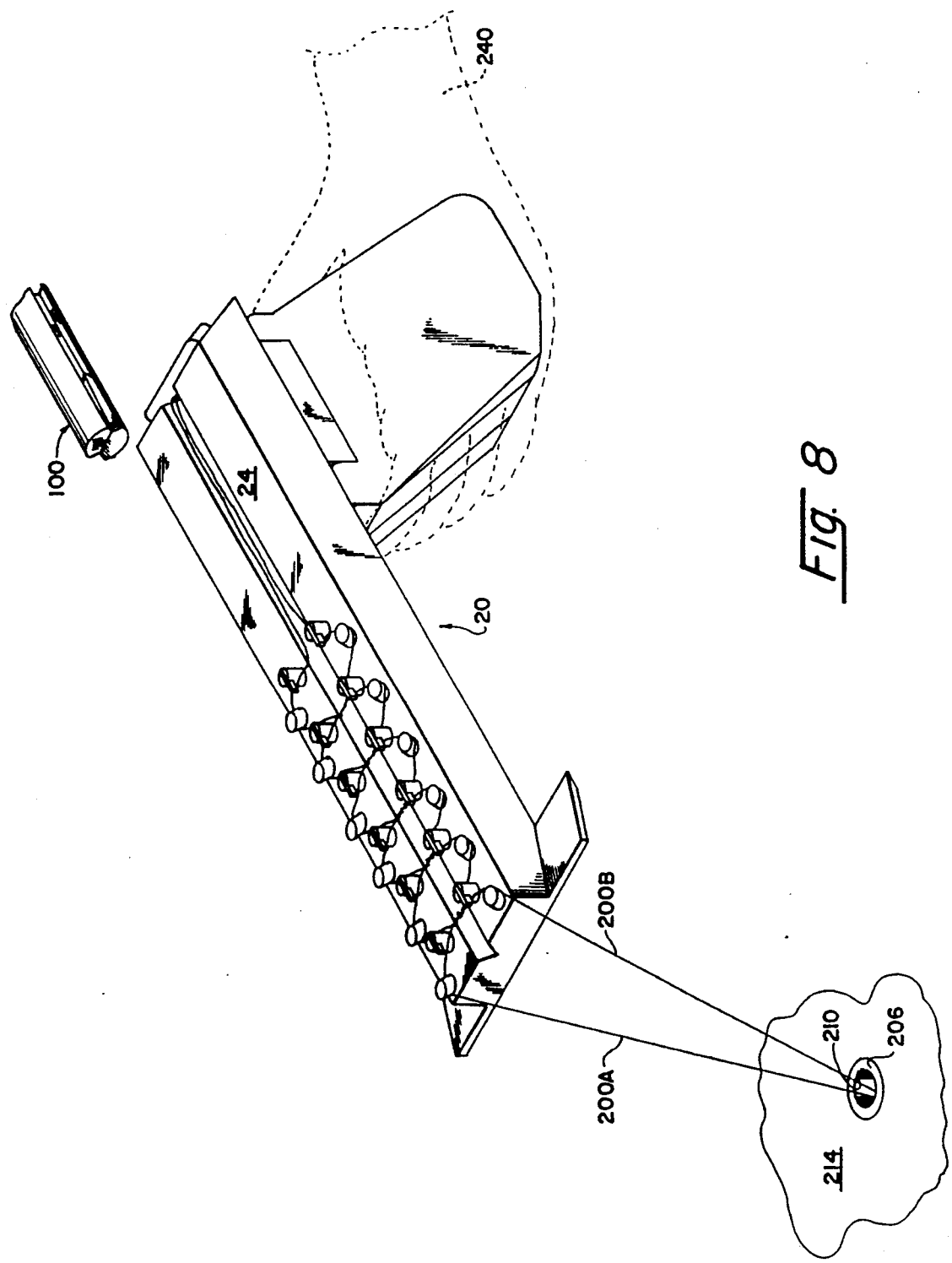
FIG. 8 is a perspective view showing lengths of suture extending from the surgical site to the suture throw support device, with the front end of the rundown tool set to engage the leading throw on the support device.
Figure 9:
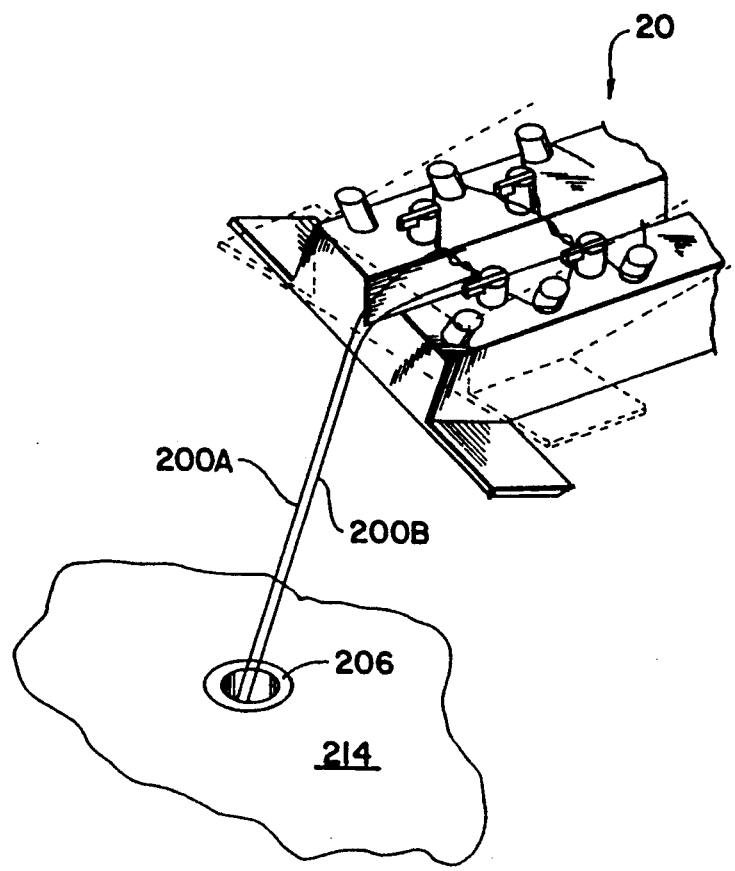
FIG. 9 is a perspective view showing the suture throw support device being manipulated to release the suture from the first two pegs on the support device.

Thereafter, the user of the suture throw holder and rundown system detaches tape 216 so as to free support device 20 from skin surface 214, moves legs 70 and 72 of support device 20 to the closed position (FIG. 3), and grips the legs in his or her hand 240 (FIG. 8). Then, the user elevates the support device slightly above surface 214 of surface tissue 208 so as to nearly eliminate the slack in the portions of suture ends 200A and 200B extending between surface 214 of upper tissue piece 208 and leading pegs 54 of first group 52A (FIG. 8). Next, the user dips and rotates support device 20 so as to disengage suture ends 200A and 200B from leading pegs 54 of group 52A (FIG. 9).

Figure 10:
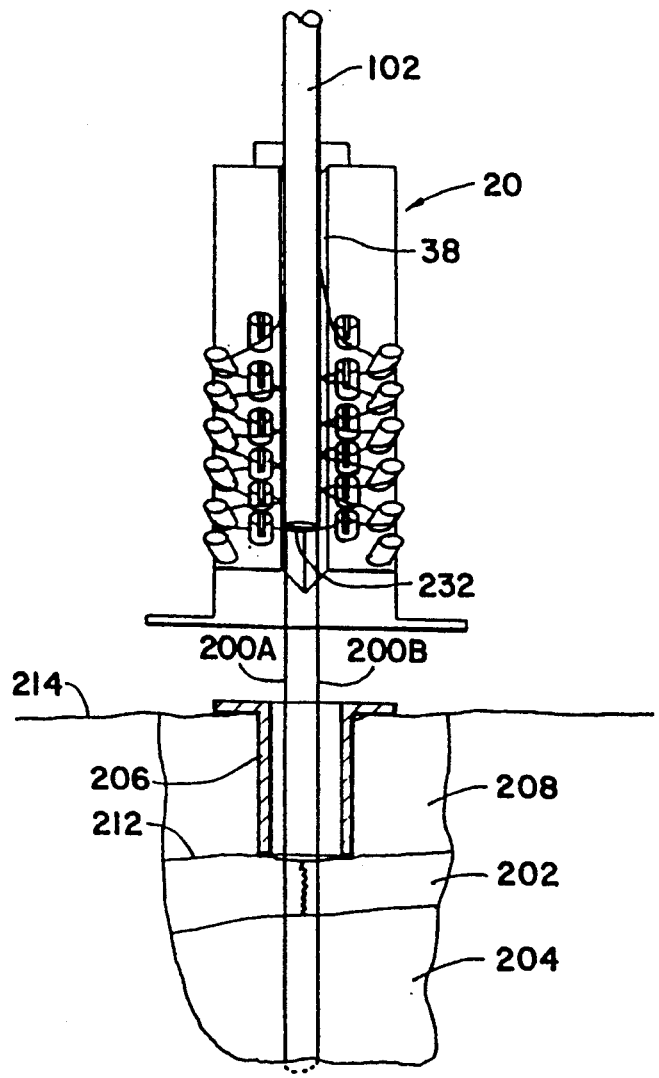
FIG. 10 is a front elevation view showing the suture throw support device elevated slightly above the opening in tissue leading to the surgical site and the leading throw captivated in the front groove of the rundown tool.

Once this has been accomplished, the user grasps handle 104 of rundown tool 100 and manipulates the latter so that first throw 232 is received in V-shaped groove 106 in shaft 102, as shown in FIG. 10. More specifically, throw 232 is positioned in V-shaped groove 106 so that the ends of suture portions 200A and 200B extending rearwardly away from the throw are received in notches 110 and at least the front portions of elongate grooves 108. See FIG. 10. Typically, tool 100 is inclined as this is done so that its long axis forms an angle θ with top surface 24 of frame 22 (FIG. 8). Preferably, angle θ is about 15°-30°. To receive throw 232 in V-shaped groove 106, the bottom portion of the front end of shaft 102 is typically inserted in groove 38 in top surface 24 immediately behind the throw. The cross-sectional size and configuration of groove 38 is chosen so that this bottom portion of shaft 102 can be accommodated in the groove. Notches 110 direct the trailing ends of the throw residing in V-shaped groove 106 into elongate grooves 108. Elongate grooves 108 in shaft 102 are provided to ensure that the portions of suture ends 200A and 200B extending rearwardly from the throw which is received in V-shaped groove 106 do not twist around the front end of shaft 102.

Figure 11:
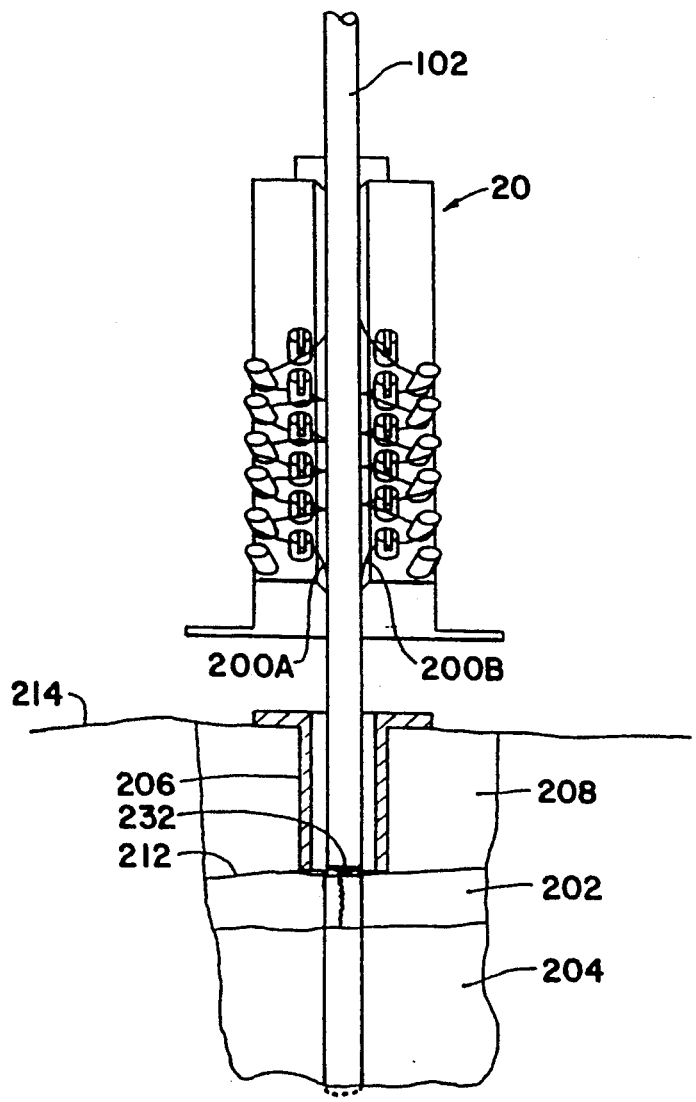
FIG. 11 is similar to FIG. 10, except that the front end of the rundown tool, and the throw captivated therein, has been moved to a position adjacent the target tissue at the surgical site.

Next, while holding support device 20 so as to maintain tension on the portions of suture extending between surface 212 of upper tissue piece 202 and first throw 232, the user uses the rundown tool 100 to push first throw 232 (received in V-shaped groove 106 in shaft 102) down the lengths of suture until the throw contacts tissue surface 212. (FIGS. 10 and 11).

Figure 11A:
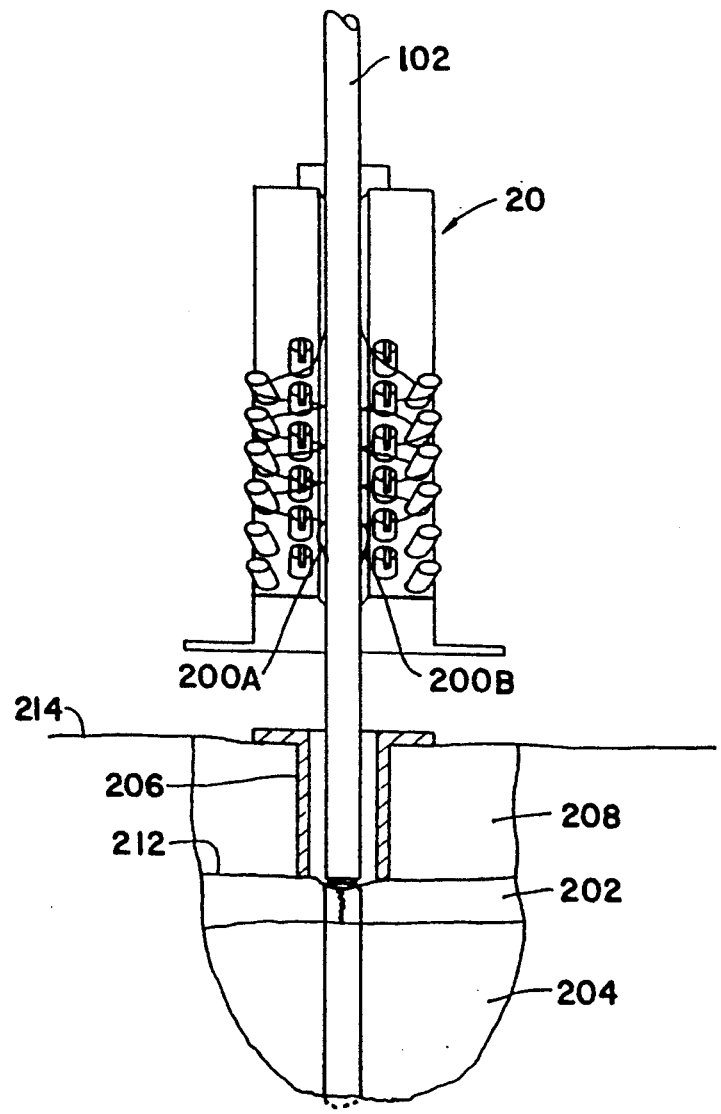
FIG. 11a is similar to FIG. 11, except that the suture device has been manipulated to release the suture from the two leading pegs of the second group of pegs.
Figure 12:
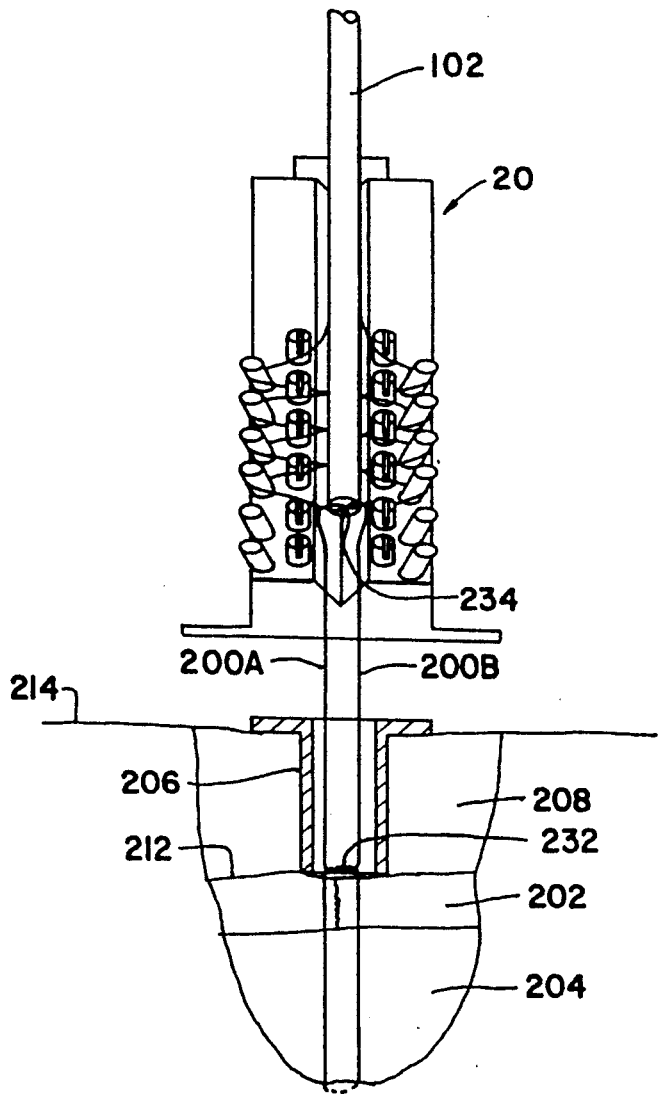
FIG. 12 is similar to FIG. 11, except that the second throw supported on the support device is captivated in the front groove in the support tool.

While holding throw 232 against tissue surface 212 with rundown tool 100, device 20 is again dipped and rotated so as to disengage suture ends 200A and 200B from leading pegs 54 of group 52B. Support device 20 is then moved away from tissue surface 214 to remove the slack in the suture ends 200A and 200B created by releasing the suture ends from the leading pegs 54 of group 52A (FIG. 11a). Rundown tool 100 is then extracted from cannula 206, and second throw 234 (FIGS. 7 and 12) is positioned in V-shaped groove 106 in shaft 102 (FIG. 12). As this is done, an upward force is preferably maintained on support device 20 so as to keep the length of suture extending between tissue surface 212 and device 20 taut. Such tautness will keep throw 232 from backing off from tissue surface 212 in the event first throw 232 is a double turn throw.

Figure 13:
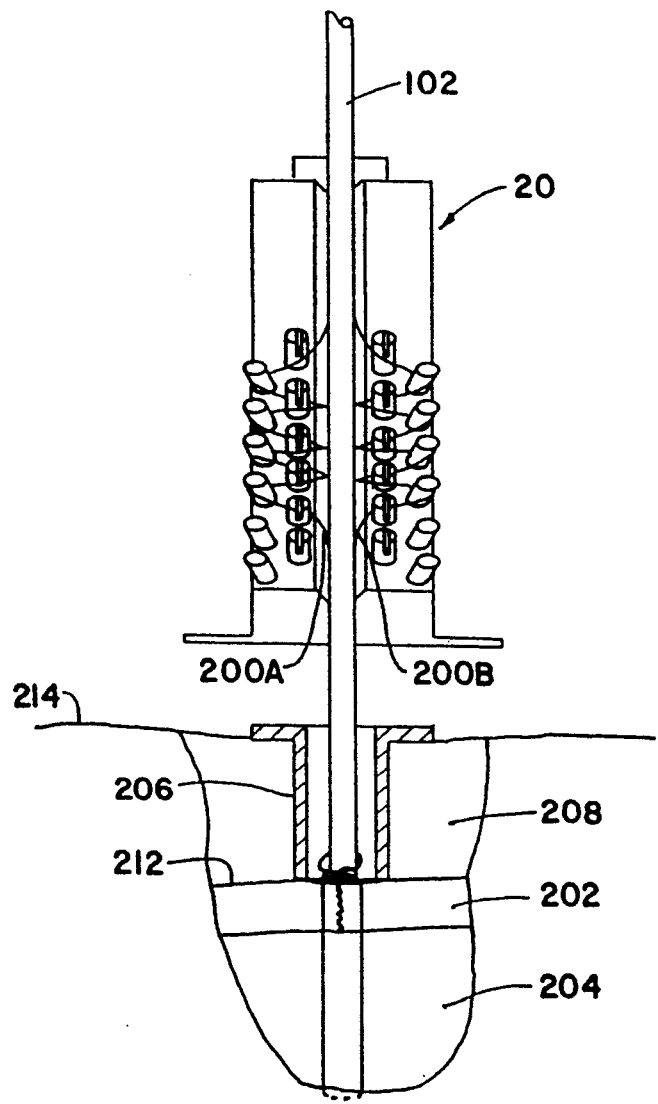
FIG. 13 is similar to FIG. 12, except that the front end of the rundown tool, and the second throw captivated therein, has been positioned at the surgical site directly above the first throw.

Next the second throw 234 is run down the suture ends until it contacts first throw 232, following the procedure described above with respect to the first throw, thereby forming a knot adjacent tissue surface 212 (FIG. 13).

Figure 14:
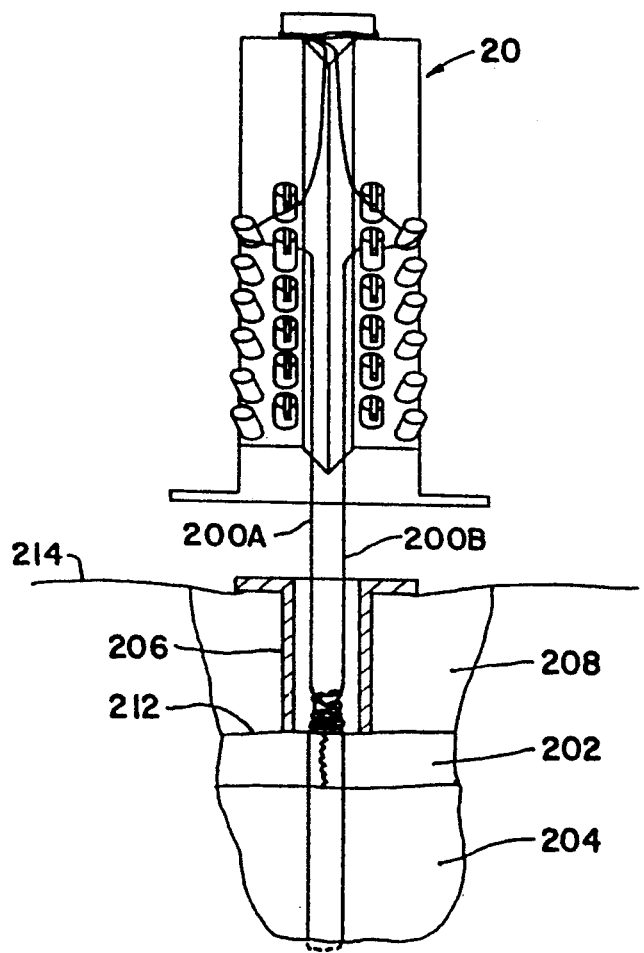
FIG. 14 is similar to FIG. 13, except that all of the throws supported on the support device have been run down to the surgical site and the rundown tool has been removed from operative association with the support device.

Thereafter, each of the remaining suture throws supported on support device 20 is run down the suture ends until it contacts the immediately preceding throw, following the procedure described above with respect to the first and second throws (FIG. 14). Finally, the ends of sutures 200A and 200B are disengaged from support device 20 and are cut off adjacent the last of the throws which was run down to the surgical site.

ALTERNATIVE EMBODIMENTS

Figure 15:
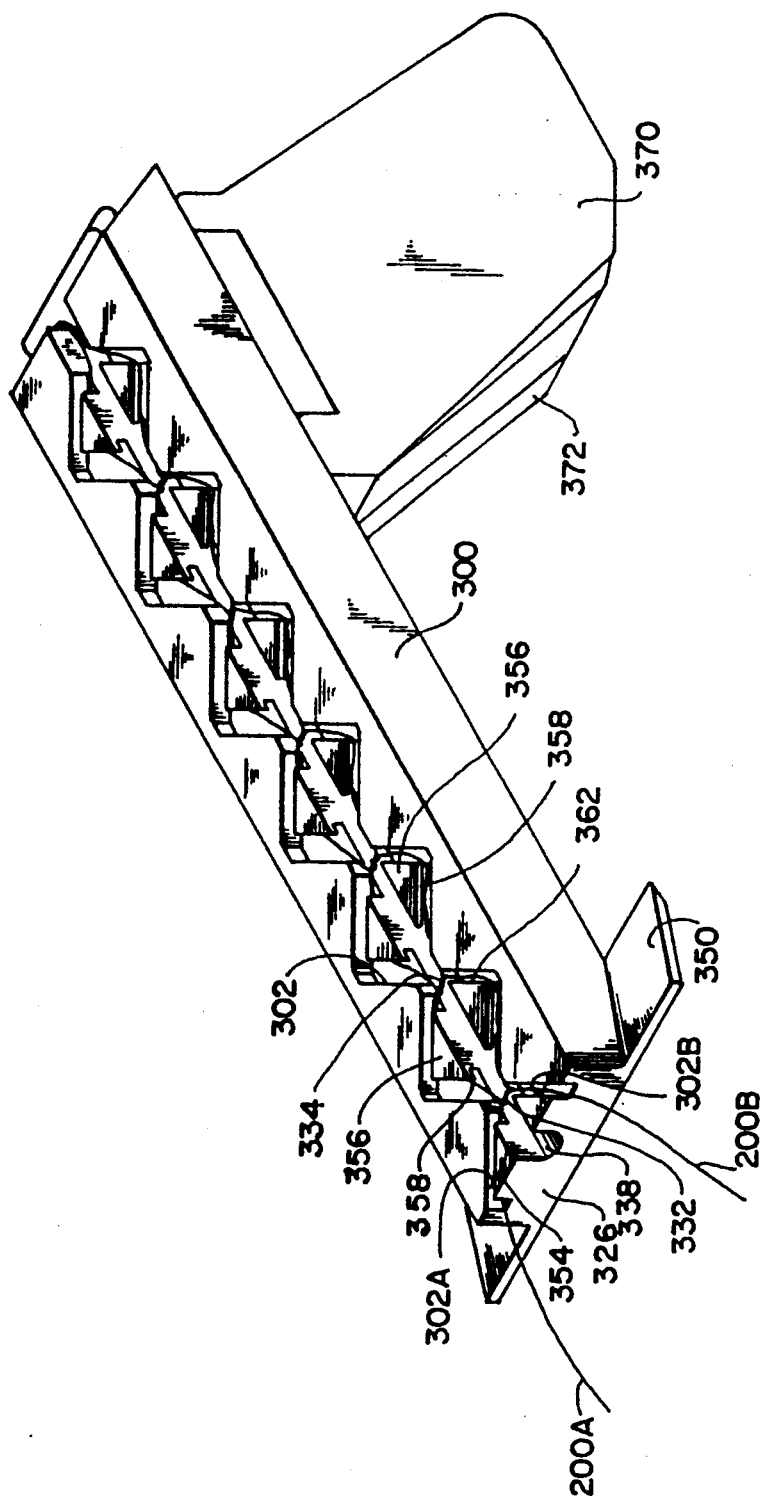
FIG. 15 is a perspective view of an alternative embodiment of the suture throw device.

Referring to FIGS. 4 and 15, in place of frame 20 with its upstanding pegs 54 and 56, support device 20 may comprise an elongate block 300 of material, such as plastic, in which a plurality of passageways 302 are provided. Passageways 302 are formed so as to define a plurality of pairs of protrusions 356, each having a finger 358 which extends away from the protrusion toward front surface 326 of the block. Passageways 302 also define a pair of leading protrusions 354 which do not include fingers 358. Protrusions 354 are provided at the front end of block 300 so as to be coextensive with front surface 326. A central passageway 338 extends between the pairs of protrusions 356. The bottom of passageway 338 is depressed below the bottom of protrusions 356.

Block 300 preferably includes a pair of front feet 350 which are substantially identical to feet 50 of frame 22. Thus, front feet 350 are secured to the front of block 300, project outwardly from the block, and are inclined at about a 30° relative to front surface 326. Block 300 also preferably includes a pair of rear legs 370 and 372 which are substantially identical to rear legs 70 and 72 of frame 22. Rear legs are pivotally attached to the rear end of block 300 so as to be movable between open and closed positions.

Suture ends 200A and 200B are threaded around protrusions 356 much like the suture ends are threaded around pegs 54 and 56 of frame 22. Specifically, suture end 200A is positioned in passageway 302A at the front of block 300 and suture end 200B is positioned in passageway 302B. Passageways 302A and 302B are formed between leading protrusions 354 and adjacent portions of block 300. After a double turn throw 332 is formed, the suture ends are wrapped around the front surfaces of the leading pair protrusions 356, under their fingers 358, and around the back surfaces 362 of protrusions 356. The portions of passageway 302 adjacent protrusions 356 are sized to permit the suture ends to be wrapped around the protrusions in this manner. Another throw 334 is formed using the suture ends 200A and 200B, and the suture ends are then wrapped around the second pair of protrusions 356, as described above with respect to the first pair. Additional throws are formed, and the suture ends are wrapped around additional protrusions, following the procedure described above. Thus, unlike frame 22, with block 300 the suture ends lead directly from one pair of protrusions 356 to the next, rather than being wrapped alternately around a leading pair of pegs 54 and a trailing pair of pegs 56.

Block 300 is used in much the same fashion as support device 20. Thus, after forming throws in the suture ends 200A and 200B and wrapping the suture ends around protrusions 356, block 300 is dipped and rotated so that the suture ends are removed from passageways 302A and 302B and are received in central passageway 338. Then, the first throw 332 is run down the suture ends to the surgical site using rundown tool 100, as described above with respect to throw 232 carried on support device 20. Subsequent suture throws are run down to the surgical site, as described above with respect to the discussion of the operation of support device 20.

In certain circumstances suture ends 200A and 200B may extend away from the surgical site through a curved passageway, e.g., an esophagus, colon, etc. Rundown tool 100 cannot be satisfactorily employed under such circumstances because it is substantially rigid. To permit suture throws to be run down a curved passageway, a flexible rundown tool 400 is provided as part of the present invention, as illustrated in FIGS. 16 and 17. Rundown tool 400 is made from a material which permits the rundown tool to flex along its length, e.g., flexcable or flextube.

Except for the fact that the rundown tool 400 is made from a flexible material, rundown tool 400 is similar to rundown tool 100, with the exception that the tool preferably comprises a spring guard 416 for ensuring suture ends 200A and 200B remain positioned in the elongate grooves 408 of the rundown tool. Thus, elements 402, 404, 406, 408 and 410 of rundown tool 400 are identical to elements 102, 104, 106, 108 and 110 of rundown tool 100.

Spring guard 416 comprises curved arms 418 and 420. One end of arm 418 is secured to shaft 402 adjacent front groove 406, and one end of arm 420 is secured to shaft 402 adjacent front groove 406 and in diametric opposition to the one end of arm 418. Arm 418 curves around shaft 402 so that its other end terminates adjacent, and covers, one of elongate grooves 408 in shaft 402. Arm 420 curves around shaft 402 so that its other end terminates adjacent, and covers, the other one of elongate grooves 408. Arms 418 and 420 both press against shaft 402 with a spring bias.

To use rundown tool 400 with spring guard 416, a suture throw is positioned in front groove 406 and then the portions of suture ends 200A and 200B extending rearwardly from groove 406 are urged between the free ends of arms 418 and 420 and shaft 402, thereby causing the arms to move away slightly from the shaft. The suture ends are then urged into elongate grooves 408, with the result that arms 418 and 420 spring back into contact with shaft 402. After the suture throw has been run down to the surgical site, and the rundown tool 400 removed from the opening leading to the surgical site, the suture ends captivated by arms 418 and 420 in elongate grooves 408 are removed by twisting shaft 402 slightly and pulling each of the suture ends out from beneath arms 418 and 420.

Knot rundown tool 100 functions satisfactorily when constant downward pressure is applied to the tool during the knot rundown procedure. However, under certain circumstances it is difficult or impossible to maintain such pressure throughout the entire knot rundown procedure. Consequently, the knot or throw may slip out of the front groove 106 of the tool. Such disengagement of the knot from the rundown tool 100 may be especially problematic when it occurs deep within the passageway leading to the surgical site.

Figure 18:
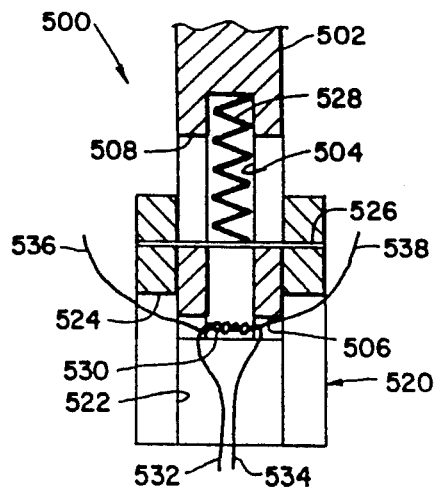
FIG. 18 is a side elevation view, taken in cross section, showing the front end of another embodiment of the rundown tool.

Referring to FIG. 18, to avoid this problem, a knot rundown tool 500 is provided as part of the present invention. Tool 500 comprises an elongate shaft 502 (only the front end of which is shown in FIG. 18) having a axial bore 504 coupled with the front end of the shaft. Shaft 502 also includes a groove 506 in the front end thereof for receiving a suture throw. Shaft 502 also includes a slot 508 extending through the central axis of the shaft perpendicular to the long axis of the shaft. Slot 508 is spaced rearwardly from front groove 506.

Rundown tool 500 also includes a sleeve 520 which surrounds the front end of shaft 502 and is mounted for axial, reciprocal movement relative to the front end of the shaft. Sleeve 520 has a hollow interior 522 sized so that shaft 502 may be received therein with a free axially-sliding fit. Sleeve 520 includes a slot 524 which extends through and perpendicular to the longitudinal axis of the sleeve and is coupled with the front end of the sleeve.

Axial movement of sleeve 520 relative to the front end of shaft 502 is limited by pin 526 which is attached to the sleeve so as to extend through the hollow interior 522 of the sleeve perpendicular to the long axis of the sleeve. Sleeve 520 is positioned relative to shaft 502 so that pin 526 is received in slot 508 in shaft 502. As sleeve 520 is moved axially relative to shaft 502, pin 526 will contact the top and bottom ends of slot 508, thereby preventing further movement of the sleeve relative to the shaft. The length of sleeve 520 and the placement of pin 526 in the sleeve are selected so that the front end of sleeve 520 will project forwardly of the front end of shaft 502 when pin 526 engages the front end of slot 508 in shaft 502, as shown in FIG. 18. When pin 526 engages the rear end of slot 508, the front end of shaft 502 will project slightly beyond the front end of sleeve 520. The orientation of pin 526 relative to slot 524 in sleeve 520 is selected to ensure the slot remains aligned with groove 506 in shaft 502 as sleeve 520 moves back and forth relative to the shaft 502.

Sleeve 520 additionally includes a spring 528 for urging pin 526, and sleeve 520 attached thereto, toward the front end of shaft 502. Spring 528 is captivated between the end of bore 504 in shaft 502 and pin 526. Spring 502 has a spring force selected so that the spring urges the pin 526 toward the front end of slot 508 with only a relatively moderate bias.

In connection with the following description of the operation of rundown tool 500, it is assumed the tool is initially in the unbiased condition shown in FIG. 18. To use the tool 500, the latter is moved toward a suture throw 530 formed from suture ends 532 and 534 emanating from a surgical site so that the throw is received in slot 524 in sleeve 520. During this movement, tension is maintained on suture portions 536 and 538. As tool 500 is moved toward throw 530 so as to cause the throw to move more deeply into slot 524, tool 500 is manipulated so that the throw is received in front groove 506 in shaft 502. When throw 530 is fully seated in front groove 506, suture portions 536 and 538 extend rearwardly away from the throw through slot 524.

After positioning the throw 530 in the front groove 506 of shaft 502, and while maintaining tension on suture portions 536 and 538, the shaft is urged toward the surgical site from which suture ends 532 and 534 emanate. This movement of the shaft 502 causes throw 530 to run down suture ends 532 and 534 toward the surgical site. As shaft 502 is urged toward the surgical site, sleeve 520 retracts (i.e. moves rearwardly) until pin 526 engages the rear end of slot 508. However, if during the course of the rundown procedure downward pressure is released from shaft 502 while still maintaining tension on suture portions 536 and 538, spring 528 will urge sleeve 520 forwardly until pin 526 engages the front end of slot 508. As a consequence of this forward movement of sleeve 520, suture throw 530 is maintained in slot 524 in the sleeve. When downward pressure is again applied to the shaft 502 the throw will be guided within the walls of slot 524 toward front groove 506 in shaft 502. Thus, with rundown tool 500, downward pressure may be temporarily released from shaft 502 without a resultant disengagement of the suture throw 530 from the rundown tool. Additionally, pin 526 ensures sleeve 520 remains rotationally aligned with shaft 502.

Figure 19:
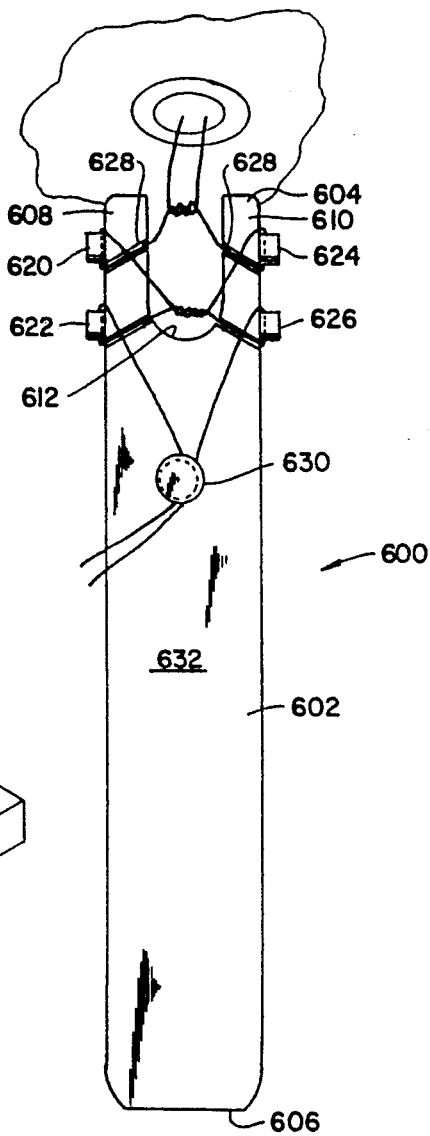
FIG. 19 is a plan view of another embodiment of the suture throw holder of the present invention shown adjacent the opening to a surgical site from which two suture ends emanate.

An important advantage of suture support devices 20 and 300 is that they permit a single individual to run a number of suture throws down to a surgical site in quick succession. However, under certain circumstances the amount of time required to lace up the suture support devices 20 and 300 with suture throws may be unacceptably large. In other cases, the surgeon may desire to only run one or two throws down to the surgical site. To avoid the need to devote a significant amount of time to lacing up the suture support device, while at the same time enjoying the benefit of a device for supporting at least one suture throw adjacent the opening to a surgical site, a suture throw holder 600, as illustrated in FIG. 19, is provided as part of the present invention.

Holder 600 comprises a flat, elongate member 602 having front and rear ends 604 and 606. Member 602 includes fingers 608 and 610 which are separated by an aperture 612. Fingers 608 and 610 are attached to one end of member 602 and terminate at the front end 604 of member 602. The width of aperture 612 is selected so that fingers 608 and 610 are spaced about 0.5" to 1.5" from one another, as measured between the inner surfaces of the fingers. Finger 608 includes pegs 620 and 622. The latter are attached to and project out from the outer surface of finger 608. Finger 610 includes pegs 624 and 626 which are attached to and project out from the outer surface of finger 610. Pegs 620 and 624 are positioned opposite one another adjacent front end 604, and pegs 622 and 626 are positioned opposite one another rearwardly of pegs 622 and 624. Each of the fingers 608 and 610 includes grooves 628 adjacent their respective pegs for receiving and directing suture, as discussed below. Grooves 628 also prevent the suture from being pinched between the inner surface of the fingers and the rundown tool. Holder 600 also includes a clamp 630 in the form of a flat plate positioned slightly above the top surface 632 of member 602 so that suture may be wedged between the plate and the top surface, thereby securing the suture to the member.

Although holder 600 has been described as comprising two pairs of pegs (i.e. pegs 620 and 622 and pegs 624 and 626), it should be appreciated that the holder may be modified to include one, three or more pairs of pegs.

Figure 20:
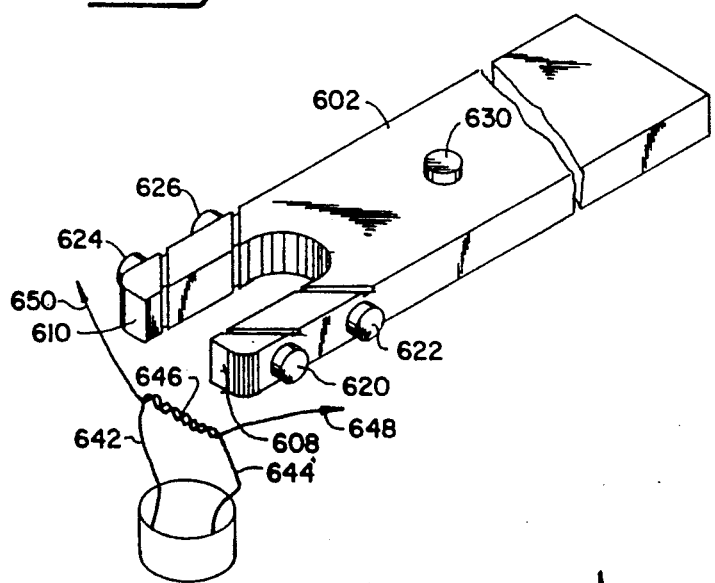
FIG. 20 is a perspective view of the holder shown in FIG. 19, with the suture ends emanating from the surgical site being formed into a surgeon's knot.
Figure 21:
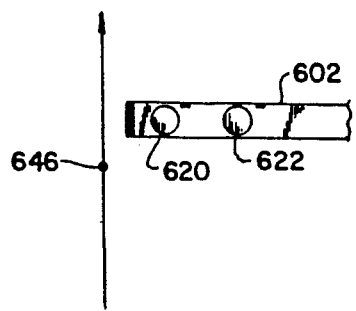
FIG. 21 is a side elevation view of the holder and suture ends shown in FIG. 20.

In connection with the following description of the operation of suture throw holder 600, reference should be made to FIGS. 19-25. For the purpose of this description, it is assumed that a length of suture has been passed through adjacent tissue pieces which are to be secured together, and the free ends 642 and 644 (FIG. 20) of the suture have been withdrawn from the surgical site. First, as illustrated in FIG. 20, a surgeon's knot 646 is formed adjacent the opening to the surgical site using suture ends 642 and 644. Then, member 602 is positioned so that its front end 604 is located adjacent the surgeon's knot 646, as shown in FIGS. 20 and 21.

Next, suture portions 648 and 650, which extend away from the surgeon's knot 646, are wrapped around front pegs 620 and 624, respectively, as illustrated in FIGS. 22 and 23. Grooves 628 formed in fingers 608 and 610 receive and direct suture portions 648 and 650 toward pegs 620 and 624. Thereafter, a single-turn throw 652 is formed in the free ends of suture portions 648 and 650 extending rearwardly from front pegs 620 and 624. Finally, the lacing procedure is completed by wrapping the free ends of suture portions 648 and 650 extending rearwardly from throw 652 around rear pegs 622 and 626, and then securing the free ends extending rearwardly from the rear pegs at clamp 630. The grooves 628 in fingers 608 and 610 adjacent rear pegs 622 and 626 receive and direct the suture portions toward the rear pegs.

The above-described lacing procedure is typically accomplished with one person holding the rear end of member 602 while a second person forms the surgeon's knot 646 and throw 652 and wraps the suture portions around the pegs 620–626. However, a single person may also perform the lacing procedure while the member 602 rests on the patient adjacent the opening to the surgical site.

To run the surgeon's knot 646 down to the surgical site, member 602 is manipulated so as to apply tension to suture ends 642 and 644 and suture portions 648 and 650, as shown in FIGS. 24 and 25. Next, a knot rundown tool 670 having a front, knot-receiving groove 672 is provided. The above-described knot rundown tools 100, 400 and 500, and knot rundown tools 700 (FIG. 26) and 800 (FIGS. 27 and 28) described hereinafter, may be satisfactorily employed as tool 670. Rundown tool 670 is then positioned so that the surgeon's knot 646 is received in its front groove 672. While maintaining tension on suture ends 642 and 644 and suture portions 648 and 650, rundown tool 670 is urged downwardly toward the surgical site. As a consequence of this movement, the surgeon's knot 646 is run down suture ends 642 and 644 to the surgical site.

Next, to run throw 652 down to the surgical site, suture portions 648 and 650 are unwrapped from front pegs 620 and 624. Rundown tool 670 is then positioned so that the throw 652 is received in groove 672. While maintaining tension on suture ends 642 and 644 and suture portions 648 and 650, rundown tool 670 is urged downwardly toward the surgical site. As a consequence of this movement, the throw 652 is run down suture ends 642 and 644 to the surgical site, typically so as to contact surgeon's knot 646. If required, additional knots or throws may be run down to the surgical site by repeating the above-described lacing and rundown procedures.

Figure 26:
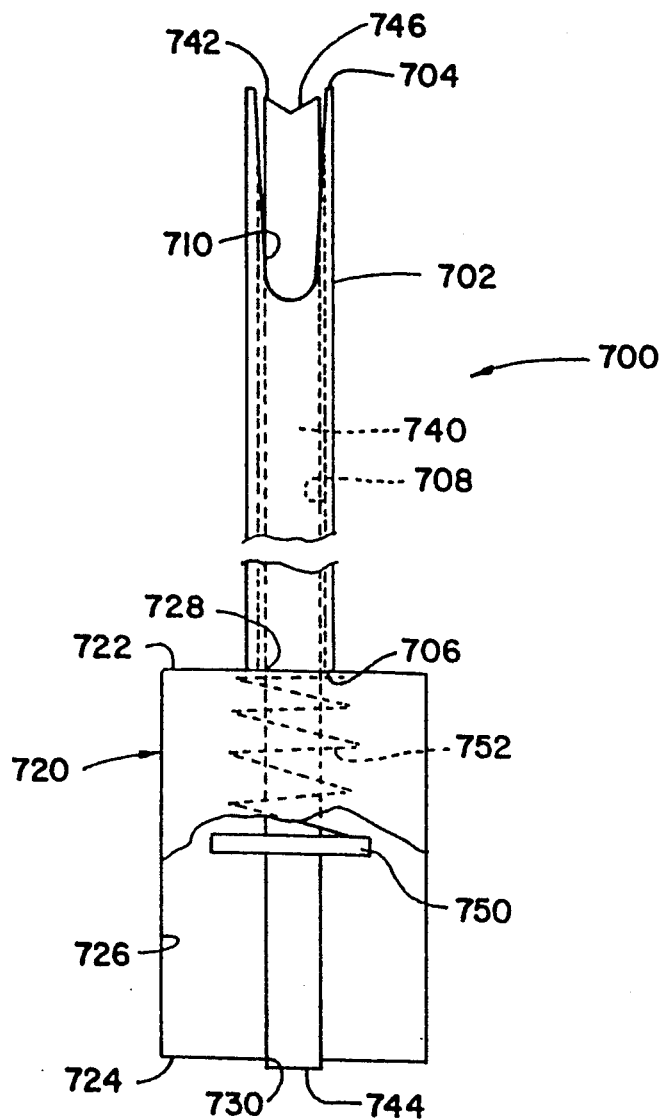
FIG. 26 is a plan view of another embodiment of the rundown tool of the present invention, with a portion of the handle of the tool being broken away to reveal the internal construction of the handle.

In yet another embodiment of the knot rundown tool, which is identified at 700 in FIG. 26, rundown tool 700 includes an elongate tube 702 having front and rear ends 704 and 706, and a hollow interior 708. Tube 702 comprises a deep groove 710 in its front end 704, which groove is sized to receive a knot or throw formed using two ends of suture.

Tool 700 also includes a handle 720 having front and back walls 722 and 724 and a hollow interior 726. Handle 720 includes a front bore 728 in front wall 722 and a rear bore 730 in rear wall 724. The diameter of bores 728 and 730 is about equal to the inside diameter of tube 702, and bores 728 and 730 are aligned with one another. Handle 720 is attached to rear end 706 of tube 702 so that the interior 708 of the tube is coupled with bore 728 in front wall 722 of the handle.

Tool 700 further includes an elongate rod 740 which is disposed in hollow interior 708 of tube 702. Rod 740 comprises front and rear ends 742 and 744, and is sized so as to slide freely along its axis in interior 708. Rod 740 also includes a groove 746 in its front end 742, which groove is sized to receive a knot or throw formed with two ends of suture. Rod 740 is sized so that when its front end 742 is adjacent the front end 704 of tube 702, as shown in FIG. 26, the rear end 744 of the tube is flush or nearly flush with the rear wall 724 of the handle, as also shown in FIG. 26.

Tool 700 additionally comprises a radially-projecting flange 750 which is attached to rod 740 at a location spaced a distance from its rear end 744 which is roughly equal to the axial depth of groove 710 in tube 702. Tool 700 also includes a coil spring 752 which surrounds rod 740 and is captivated between flange 750 and the inside surface of front wall 722 of handle 720. When rod 740 is urged forward, as shown in FIG. 26, a bias is applied to spring 752. When rod 740 is released, the bias in spring 752 urges flange 750, and rod 740 attached thereto, rearwardly until the flange contacts the inside surface of rear wall 724 of handle 720. In this unbiased state, the front groove 746 of rod 740 is positioned just rearwardly of the base of groove 710 in tube 702, and the rear end 744 of the rod projects outwardly past rear wall 724 of handle 720.

In connection with the following description of the operation of rundown tool 700, it is assumed the tool is initially in the unbiased state described above. To use the tool 700, the latter is moved toward a suture throw formed from suture ends emanating from a surgical site so that the throw is received in groove 710 in tube 702. After positioning the suture throw in the front groove 710 of tube 702, and while maintaining tension on suture ends emanating from the surgical site, tool 700 is urged toward the surgical site. This movement of the tool 700 cause the throw to run down the suture ends toward the surgical site. Once the throw is positioned at or adjacent the surgical site, rod 740 is urged forward by pressing on its rear end 744. As rod 740 moves forward relative to tube 702, the suture throw in groove 710 of tube 702 is picked up in groove 746 in rod 740 and carried forward. This forward movement of the throw tightens the throw and disengages the throw from the tube 702.

Figure 27:
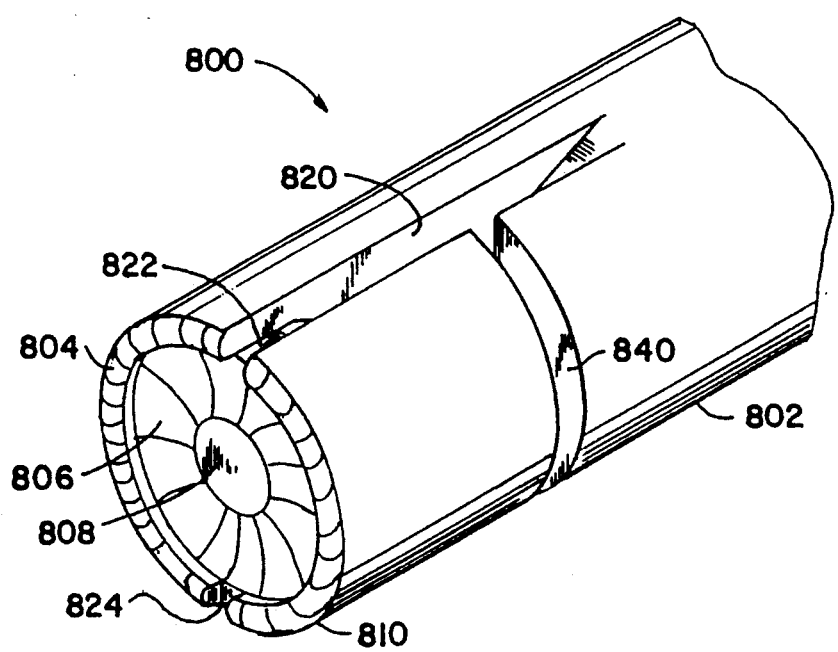
FIG. 27 is a perspective view of the front end of another embodiment of the rundown tool of the present invention.
Figure 28:
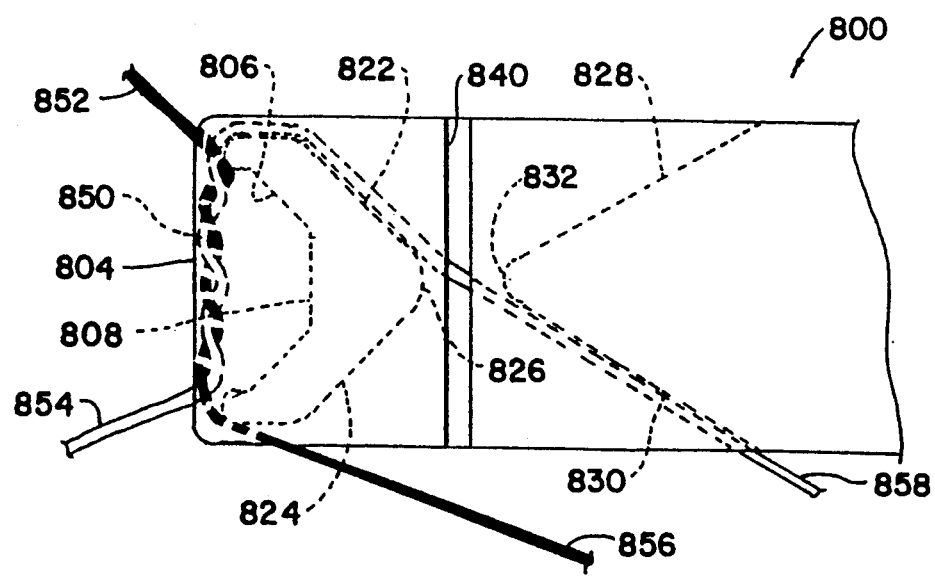
FIG. 28 is a side elevation view of the rundown tool shown in FIG. 27, with a surgeon's knot formed using the ends of suture emanating from a surgical site being positioned in the front groove of the rundown tool.

Another embodiment of the knot rundown tool 800 is shown in FIGS. 27 and 28. A front end 804 of a shaft 802 includes a frusto-conical depression 806. The diameter of depression 806 is less than the outside diameter of the front end 804 of shaft 802, whereby an annular land 810 extends around the peripheral portion of the front end of the shaft.

Shaft 802 additionally comprises a chamber or cavity 820 having parallel side walls which extend parallel to the axis of the shaft. Cavity 820 includes diametrically-opposed grooves 822 and 824 which intersect annular land 810. Grooves 822 and 824 extend rearwardly from annular land 810, initially parallel to the longitudinal axis of shaft 802, and then as they continue rearwardly the grooves penetrate more deeply into shaft 802 until they eventually meet at location 826 (FIG. 28). Cavity 820 further includes diametrically opposed grooves 828 and 830 which taper inwardly towards the central axis of shaft 802 as they extend toward the front end 804 of the shaft. Grooves 828 and 830 eventually meet at point 832 (FIG. 28). As such, the portion of cavity 820 between positions 826 and 832 extends entirely through the shaft, perpendicular to the axis of the shaft.

Shaft 802 additionally comprises a slot 840 which extends transversely, typically perpendicular to, the longitudinal axis of shaft 802. Slot 840 intersects the opening in cavity 820 between portions 826 and 832 and has a width just slightly greater than the outside diameter of the suture material to be used with rundown tool 800.

To use tool 800, the latter is moved toward a surgeon's knot (or single-turn throw) 850 formed using suture ends 852 and 854 emanating from a surgical site so that the surgeon's knot is received in frusto-conical depression 806 and the front end 804 of the shaft. Shaft 802 is manipulated so that suture portions 856 and 858 extending rearwardly from surgeon's knot 850 are received in front grooves 824 and 822 respectively. Suture portion 858 is then inserted into slot 840 so as to initially be received in the portion of cavity 820 between portions 826 and 832. Then, suture portion 858 is tensioned so as to extend along the sloping portions of front groove 822 and rear groove 830. Thereafter, suture portions 856 and 858 are lead rearwardly from the front end 804 of shaft 802.

Next, while maintaining tension on suture ends 852 and 854 emanating from the surgical site and suture portions 856 and 858 extending rearwardly away from the front end 804 of shaft 802, tool 800 is urged downwardly toward the surgical site. This movement of the tool 800 causes the surgeon's knot 850 to run down the suture ends 852 and 854 toward the surgical site. Once the surgeon's knot 850 is positioned at or adjacent to the surgical site, shaft 802 is pulled rearwardly away from the surgical site. During this rearward movement, suture portion 858 is drawn through cavity 820. If desired, tool 800 may be moved rearwardly until the free end of suture portion 858 passes through and out of cavity 820. Alternatively, the rundown tool may be extracted rearwardly a distance such that the tool is no longer positioned in the opening leading to the surgical site. Thereafter, suture portion 858 may be extracted from shaft 802 via slot 840, thereby eliminating the need to run the entire length of suture portion 858 through cavity 820.

The suture holder, rundown tool and cutter system embodying the present invention is characterized by a rundown tool of the type hereinbefore described in combination with a cutter, means being provided for guiding the cutter to a position for severing the suture ends adjacent the knot. A specific embodiment of a rundown tool and cutter system embodying the present invention is denoted by the reference character 900 in FIGS. 29 and 30. Rundown tool and cutter system 900 includes a suture knot rundown tool 902 and a cutter assembly 904. Suture knot rundown tool 902 includes a shaft 906 and a handle 907 that is attached about the shaft adjacent to the back end of the tool. In one embodiment, shaft 906 has a frusto-conical depression 908 at a front end thereof. The diameter of depression 908 is less than the outside diameter of shaft 906, whereby an annular land 910 extends around the peripheral portion of the front end of the shaft.

Shaft 906 additionally comprises a central bore 920 having parallel side walls which extend parallel to the axis of the shaft. Diametrically-opposed grooves 922 and 924 at the front end of rundown tool 902 intersect annular land 910. Grooves 922 and 924 extend rearwardly from annular land 910, parallel to the longitudinal axis of shaft 906.

Shaft 906 additionally comprises a pair of longitudinal, diametrically-opposed slots 928 and 930, and a transverse slot 940. Slots 928 and 930 are parallel to the longitudinal axis of shaft 906 and slot 940 is perpendicular to the longitudinal axis of shaft 906. Slot 940 intersects or communicates with both slots 928 and 930. The width of slots 928, 930 and 940 are just slightly greater than the outside diameter of the suture material to be used with rundown tool 900. Central bore 920 defines a guideway for cutter assembly 904. If desired, the central bore 920 may extend the entire length of the shaft 906, and depression 908 may simply comprise the distal end of bore 920.

Figure 32:
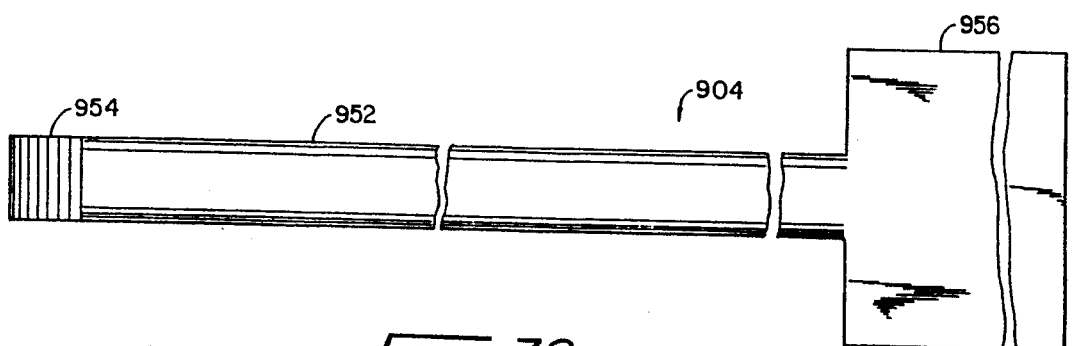
FIG. 32 is a side elevation of the cutter shown in FIG. 30.

Referring now to FIG. 32, it will be seen that cutter assembly 904 includes an elongated shaft 952 having a sharp cutting blade 954 at a front end.

The configuration of cutting blade 954 is deemed to be both significant and important. In the normal course of events, blade 954 will adequately trim the free suture ends. It is subject, however, to being nicked and/or dulled by contact with other objects, being dropped, or damaged during the insertion process into bore 920 of rundown tool 902. The open (i.e., unguarded) nature of the blade 954 also represents a risk for injury to operating room staff and to patients. Further, the thin configuration of blade 954 creates a certain level of probability that the free suture ends will not be trimmed as desired because the knife edge may slip between them rather than engaging and severing them.

In response to these concerns, the present invention provides cutting blade configurations such as those shown in FIGS. 35–41, in which like reference numerals refer to like elements throughout. As will be seen with reference to FIG. 35, at least two shoulder members 1001 project from the front end of shaft 952. Shoulders 1001 are of equal height and are located adjacent to the periphery of the front end of shaft 952 at equally spaced circumferential intervals relative to each other. Cutting blades 1000 are formed in the front end of shaft 952 typically by grinding or machining the shaft 952 adjacent its front end to form the blade edge(s). In the broadest sense, a separate blade 1000 extends radially toward the longitudinal axis of the shaft 952 from the base 1002 of each shoulder 1001. Further, depending upon the shoulder dimensions chosen, any number of shoulders may be used. Practically, however, it has been found that four shoulders is the maximum for convenient fabrication and to assure that suture will fit between the various shoulder pairs to engage the blades during the trimming operation.

Figure 37:
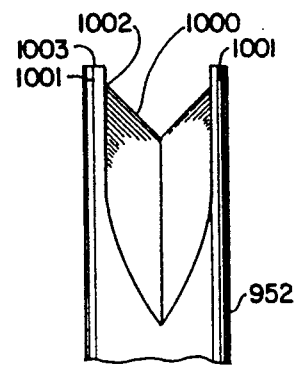
FIG. 37 is a side elevation of yet another alternative forward end of the cutter.
Figure 38:
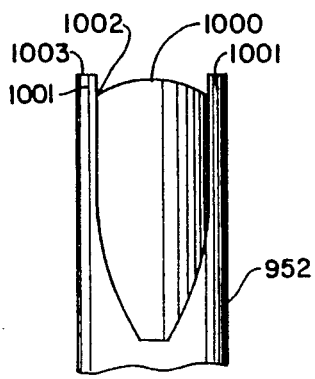
FIG. 38 is a side view of still another alternative forward end of the cutter.
Figure 39:
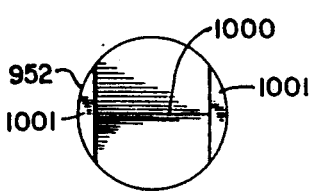
FIG. 39 is a representative end view applicable to each of the alternative forward ends of the cutter shown in FIGS. 35-38.
Figure 40:
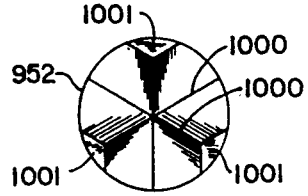
FIG. 40 is an end view of yet another forward end of the cutter.
Figure 41:
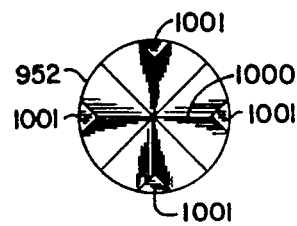
FIG. 41 is an end view of still another forward end of the cutter.

The blades 1000 extending inwardly from the shoulders form a single blade edge in the two shoulder case as shown in FIGS. 35–39. Also, the blades 1000 may be formed to extend normally from the base of the shoulders or to curve or taper distally or proximally therefrom as they extend toward the longitudinal axis of shaft 952. The result in each case is a single blade edge extending between the shoulders, but that edge may be straight as in FIG. 36, concavitively curved as in FIG. 35, convexedly curved as in FIG. 38, or V-shaped as shown in FIG. 37. The exact blade configuration chosen will depend upon factors such as suture type and blade severing characteristics. For example, a braided suture may be less easily severed than a single filament and/or the sutured tissue may vary in the extent to which it can withstand the twisting forces applied to the knot by the cutting operation. In such cases, a curved or V-shaped blade may be preferred because of its greater cutting surface engagement with the suture.

Similarly, the cutting blade configuration is not intended to be limited to a single blade. For example, in the event that three or four shoulders are used, separate blades extend from the base of each shoulder as representatively shown in FIGS. 40 and 41. These blades may meet at the longitudinal axis of the shaft 952 or at another axis parallel thereto as desired for any particular usage context.

It will be seen therefore, that the shoulders act as blade guards. As long as the entire cutting blade configuration is located proximally of the distal end 1003 of the shoulders, and adequate space is provided between the various shoulder pairs for suture passage, the cutting means of the invention will function as intended.

A handle 956 is attached to a back end of shaft 952. The rear surface 956A of handle 956 (FIG. 29) may be contoured to facilitate pushing the blade(s) against the sutures. Similarly, it has been found that the desired angle of blade engagement with the sutures may be assured by providing handles 907 and 956 with the same axial cross-sectional shape, and affixing shaft 952 to handle 956 such that blade(s) 1000 pass through the slotted portion of shaft 906 at the desired angle to suture extending between slots 928 and 930 when the distal end of handle 956 is brought against the proximal end of handle 907 with their geometric cross-sections aligned (see FIGS. 29 and 30).

Figure 29:
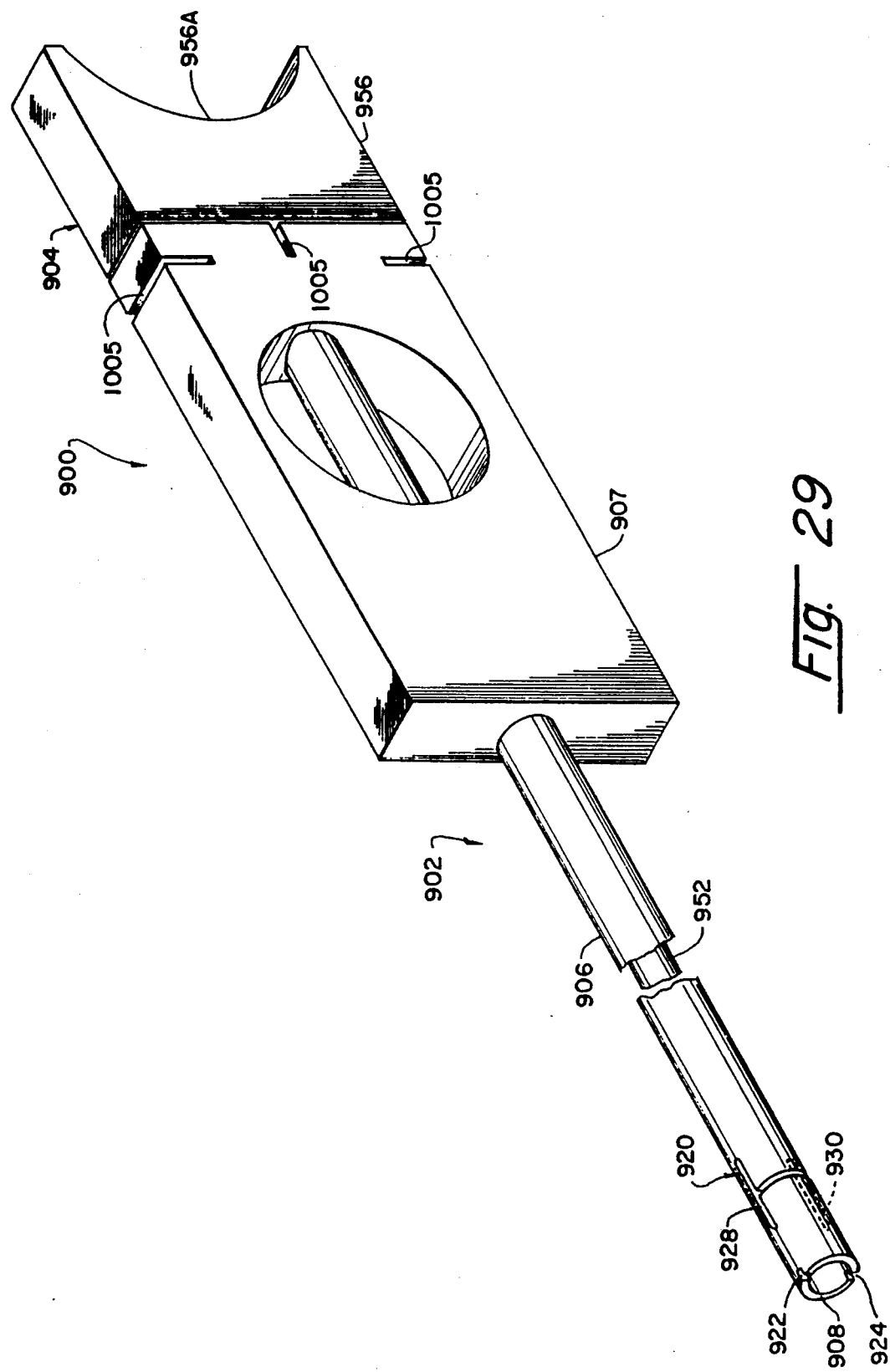
FIG. 29 is a perspective view in side elevation of the rundown tool and cutter system embodying the present invention.
Figure 30:
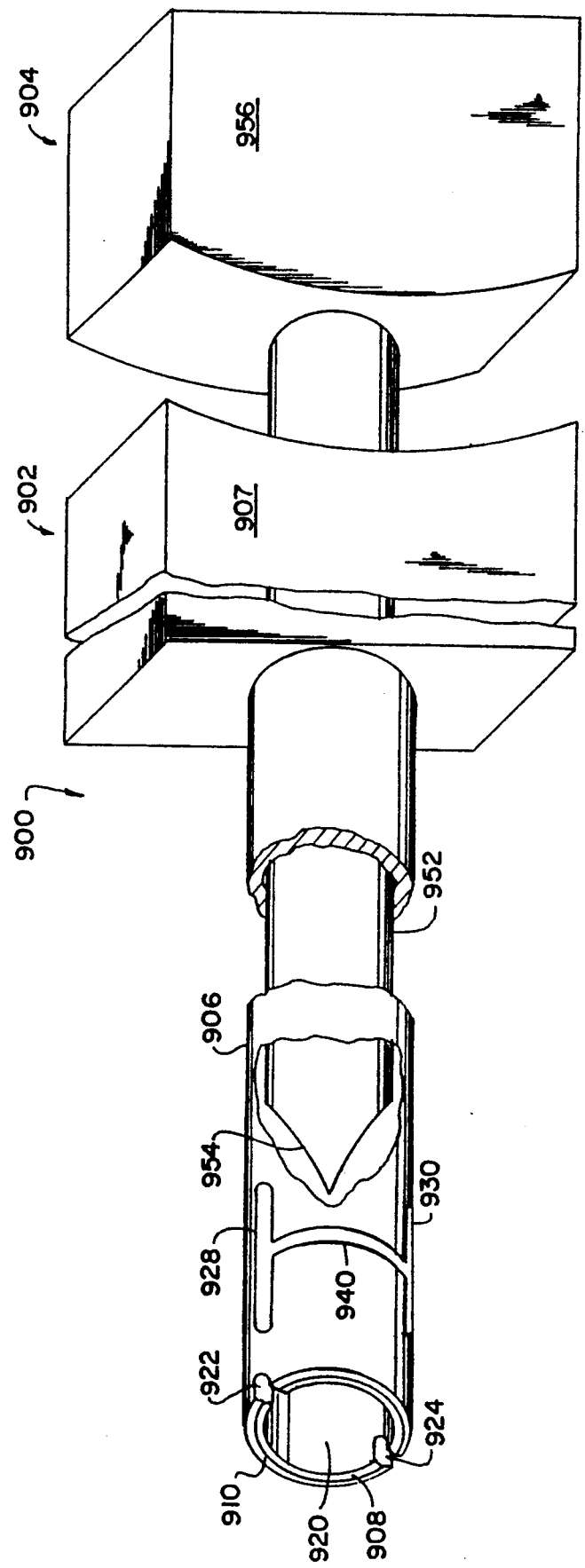
FIG. 30 is a perspective view in side elevation, partly broken-away, of the rundown tool and cutter system shown in FIG. 29.
Figure 31:
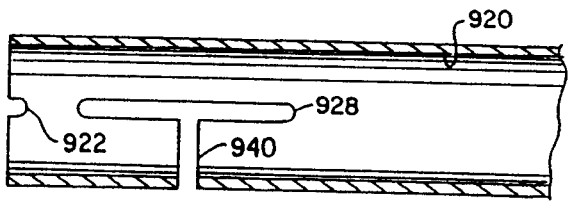
FIG. 31 is a side elevation in section of the rundown tool and cutter system shown in FIG. 29.

Alternatively, as illustratively shown in FIG. 42, handle 956 may be provided with a similar, but slightly larger, axial cross-sectional shape to that of handle 907. Flanges 956B extend distally from handle 956 forming a cavity 956C having substantially the same axial cross-sectional shape as handle 907. In the embodiment shown, cavity 956C is a slot adapted to receive the proximal end 907A of handle 907. The desired angle of blade engagement with the sutures again is assured by affixing shaft 952 to handle 956 such that blade(s) 1000 pass through the slotted portion of shaft 906 at the desired angle to suture extending between slots 928 and 930 when the distal end 956D of handle 956 is brought against the proximal end 907A of handle 907. The need for handle 907 to slide between flanges 956B in order to be brought against the distal end 956D of handle 956 assures the positive alignment of shafts 906 and 952 during the severing operation. In addition, by selecting the distance flanges 956B extend distally from handle 956 appropriately, the desired alignment of shafts 906 and 952 may be assured at a point during the insertion of shaft 952 into shaft 906 well prior to the point at which cutting blade(s) 1000 engage the suture extending between slots 926 and 930. Such positive interengagement of the rundown and cutter tools has obvious advantages. This is particularly in cases wherein the operator of the system is concentrating on the condition of his patient and the overall progress of the surgical procedure, and may not take the care required to align the planar geometric shapes of the distal end of handle 956 and the proximal end of handle 907 as shown in FIG. 29.

The provision of suture retention means such as slots 1005 in handle 907 also may be desired, particularly to facilitate the maintenance of tension on the free suture ends during the trimming operation. Slots 1005 may be sized so that they make a relatively close fit with the suture, whereby relatively few turns of the suture in slots 1005 will be needed to secure the free suture ends to the handle, or slots 1005 may be sized so that they make a relatively loose fit with the suture, whereby relatively more turns of the suture will be needed to secure the free suture ends to the handle. Preferably, at least two of the slots 1005 extend perpendicular to the longitudinal axis of the handle and are in alignment with one another, as shown in FIG. 29, so that suture turns can extend from one of these slots to the other. Preferably at least one other slot 1005 is also provided, this slot being formed in the rear end of handle 907 and extending parallel to the longitudinal axis of the tool, so that suture exiting the front end of the tool can extend straight back into this slot if desired. Shaft 952 is sized and shaped to be slidably received in central bore 920. The length of shaft 952 is such that blade 954 will extend at least to the distal end of slots 928 and 930 without extending beyond the front edge of rundown tool 902 when rundown tool handle 907 and cutter handle 956 are together.

Figure 33:
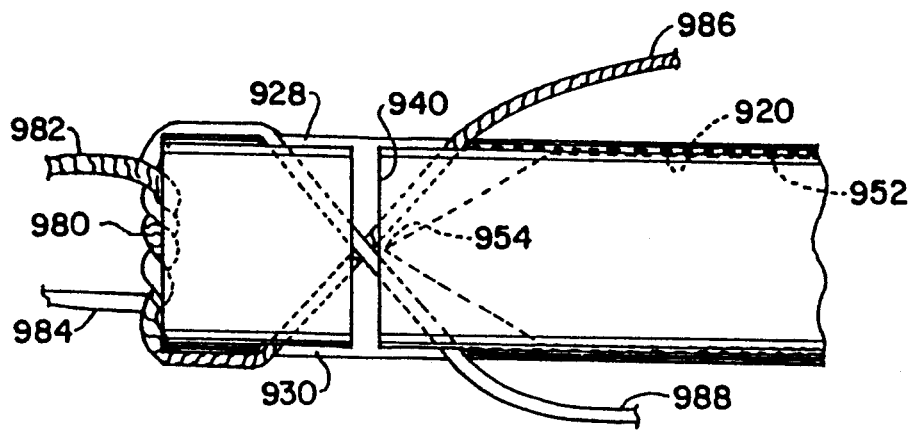
FIG. 33 is a side elevation of the rundown tool and cutter system shown in FIG. 29 with a surgeon's knot being positioned in a front groove thereof, the ends of the suture exiting on opposite sides.

To use tool 900, knot rundown tool 902 is moved toward a knot (or single-turn throw) 980 (FIG. 33) formed using suture ends 982 and 984 emanating from a surgical site so that the knot is received in the front end of the shaft 906. Shaft 906 is manipulated so that suture portions 986 and 988 extending rearwardly from the knot 980 are received in front grooves 924 and 922, respectively. Suture portions 986 and 988 are then inserted into slot 940 so as to initially be received in the portion of bore 920. Then, suture portion 988 is tensioned so as to extend along the front slots 928 and 930. Thereafter, suture portions 986 and 988 are lead rearwardly from the front end of shaft 906.

Figure 34:
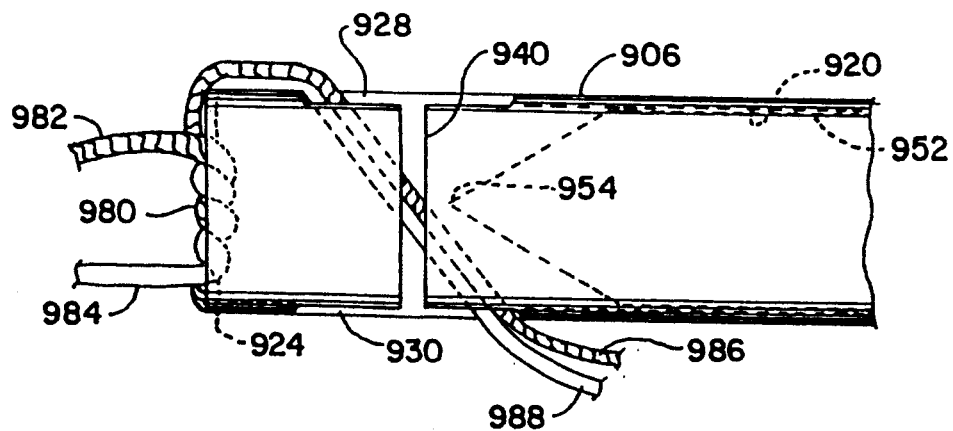
FIG. 34 is a side elevation of the rundown tool and cutter system shown in FIG. 29 with a surgeon's knot being positioned in a front groove thereof, the ends of the suture existing on the same side.
Figure 35:
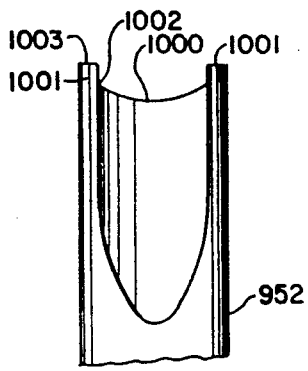
FIG. 35 is a side elevation of an alternative forward end of the cutter.
Figure 36:
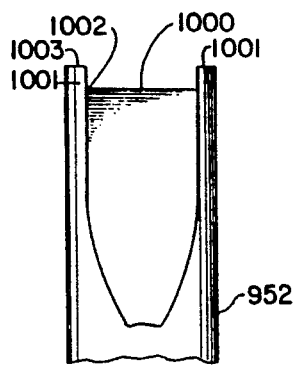
FIG. 36 is a side elevation of another alternative forward end of the cutter.

Next, while maintaining tension on suture ends 982 and 984 emanating from the surgical site and suture portions 986 and 988 extending rearwardly away from the front end of shaft 906, tool 902 is urged downwardly toward the surgical site. This movement of the tool 902 causes the knot 980 to run down the suture ends 982 and 984 toward the surgical site. The procedure continues until the surgeon has made a knot with the desired number of throws. Then, cutter assembly 904 is inserted into central bore 920 and pushed downwardly in the central bore which lies in a path that intersects suture ends 986 and 988 above the knot. Blade 954 blindly severs suture ends 986 and 988 at substantially the same length every time adjacent the knot. Suture ends 986 and 988 are blindly severed closer to the knot at substantially equal lengths when the suture ends pass out the same side of tool 902 as shown in FIG. 34. Once suture ends 986 and 988 have been severed tool 902 and cutter 904 are extracted from the surgical site.

An important advantage of the present invention is that it permits a number of throw (formed using suture ends extending from a remote surgical site) to be laced onto a holding device at a location remote from the surgical site, and then quickly and easily run down the suture ends to the surgical site so as to form a multiple throw knot at the surgical site, substantially without damaging the tissue in which the suture is positioned. Then, while the knot rundown tool 902 is in place, the suture ends are blindly cut at substantially equal lengths every time adjacent the knot.

Since certain changes may be made in the above disclosure without departing from the scope of the invention herein involved, it is intended that all matter contained in the above description and shown in the accompanying drawings be construed in an illustrative and not in a limiting sense.

What is claimed is:

1. A suture throw rundown and cutter tool for running a throw down loose ends of a suture extending from a surgical site, and for severing the loose ends of the suture, said tool comprising:
   (a) rundown tool means for engaging adjacent a surgical site a throw formed using two ends of suture extending from the surgical site and running said throw down said two ends of the suture to said surgical site to form a knot, said rundown tool means including a first elongate shaft having a distal end, a proximal end, a longitudinal bore extending the entire longitudinal length of said first shaft, throw engagement means located at the distal end of said first shaft, an throw position maintenance means extending through said first shaft proximally of said distal end, said maintenance means being adapted for the slideable passage of said loose suture ends therethrough; and
   (b) cutter means for cutting the suture ends adjacent said knot, said cutter means including a second elongate shaft having distal and proximal ends and adapted for telescopic engagement with said bore of said first shaft, at least two shoulder members extending distally from the distal end of said second shaft, said shoulder members being located in equally spaced circumferential relation to each other adjacent to the periphery of said distal end of said second shaft, and cutting blade means formed in the distal end of said second shaft extending radially inwardly from each of said shoulder elements.

2. A tool according to claim 1 wherein said cutter means includes two shoulder members, and the cutting blade means form a single cutting edge disposed substantially normal to the longitudinal axis of said second shaft.

3. A tool according to claim 1 wherein said cutter means includes two shoulder members, and the cutting blade means also extend proximally of said distal end of said second shaft along corresponding curves to form a single curved blade.

4. A tool according to claim 1 wherein said cutter means includes two shoulder members, and the cutting blade means also gradually taper proximally from said front end of said second shaft to form a single generally V-shaped blade.

5. The tool according to claim 1 wherein said cutter means includes three shoulder members, and the cutting blade means meet at the longitudinal axis of said second shaft.

6. The tool according to claim 1 wherein said cutter means includes four shoulder members, and the cutting blade means meet at the longitudinal axis of said second shaft.

7. The tool according to claim 1 wherein said rundown means includes a first handle having a predetermined longitudinal geometric cross-section affixed about said first shaft adjacent to its proximal end, said cutter means includes a second handle having a longitudinal geometric cross-section corresponding to the longitudinal geometric cross-section of said first handle affixed to the proximal end of said second shaft such that when the second shaft is telescoped into said first shaft and the cross-sections of the first and second handles are held in longitudinal alignment, the orientation of the cutting blade means is optimized relative to said loose suture ends.

8. The tool according to claim 7 wherein said first handle includes suture retention means adapted to maintain tension on the loose suture ends during the operation of the cutting means.

9. The tool according to claim 8 wherein said suture retention means comprises slots formed in the first handle having a width slightly smaller than the diameter of the suture.

10. The tool according to claim 1 wherein the combined longitudinal length of said second shaft and said shoulders is less than the longitudinal length of said first shaft but greater than the distance between the proximal end of said first shaft and the throw position maintenance means.

11. A tool according to claim 1 wherein said throw position maintenance means comprises longitudinal slot means and transverse slot means located proximally of said front end, said transverse slot means intersecting said longitudinal slot means, the width of each of said longitudinal slot means and said transverse slot means being greater than the outside diameter of the suture ends.

12. A tool according to claim 11 wherein said longitudinal slot means includes diametrically-opposed slots, said transverse slot extending between and intersecting said longitudinal slots.

13. The tool according to claim 1 including loose suture end retention means located adjacent to the proximal end of said first shaft.

14. The tool according to claim 1 wherein said rundown means includes a first handle having a predetermined longitudinal geometric cross-section affixed about said first shaft adjacent its proximal end, said cutter means includes a second handle defining a distally facing cavity having a longitudinal geometric cross-section substantially corresponding to the longitudinal geometric cross-section of said first handle affixed to the proximal end of said second shaft such that when said second shaft is telescoped into said first shaft and the proximal end of said first handle is received in said distally facing cavity of said second handle, the orientation of the cutting blade means is optimized relative to said loose suture ends.

15. The tool according to claim 14 wherein said distally facing cavity is a slot.

16. A method of running throws formed using two loose ends of suture extending from a tissue surface in a surgical site down the loose ends of the suture to the tissue surface to form a knot at the surgical site, and blindly cutting the loose ends of the suture to substantially the same length every time adjacent the knot, the method comprising the following steps:

(a) providing a suture throw rundown and cutter tool comprising:

(i) rundown tool means for engaging a throw formed using two ends of suture extending from a surgical site and running said throw down said two ends of suture to said surgical site, said rundown tool means comprising a first elongate shaft having (1) a front end, said front end including a first groove sized to receive a throw formed using two loose ends of suture extending from a surgical site, with said first groove having a bottom portion, (2) a longitudinally extending bore formed in said shaft, said bore extending the entire length of said rundown device, and (3) throw maintenance means extending through said first shaft proximally of its front end, said throw maintenance means adapted to removeably and slideably receive said loose suture ends therethrough; and (ii) cutter means slidably received in said bore, said cutter means including (1) a second elongate shaft having distal and proximal ends and adapted for telescopic engagement with said bore of said first shaft, (2) at least two shoulder members extending distally from the distal end of said second shaft, said shoulder members being located in equally spaced circumferential relation to each other adjacent to the periphery of said distal end of said second shaft, and (3) cutting blade means formed in the distal end of said second shaft extending radially inwardly from each of said shoulder elements;

(b) providing a throw in two loose ends of suture extending from a tissue surface in a surgical site, and tensioning the two loose ends of suture extending away from said throw;

(c) manipulating said first shaft and said loose suture ends so that said throw is received in, and engages the bottom portion of, said first groove, and said loose suture ends are slideably received in said throw maintenance means;

(d) urging said first shaft toward said tissue surface, while maintaining engagement of said throw with said bottom portion of said first groove, so as to cause said throw to run down said lengths of suture until said throw is positioned adjacent said tissue surface; and (e) repeating steps (b) though (d) to place a second throw atop the first throw so as to form a knot at the surgical site; and (f) guiding said cutter means down said bore and blindly cutting the portion of the respective suture ends extending through said throw maintenance means.

17. A method as claimed in claim 16 wherein the suture ends are cut at substantially equal lengths.

18. The method according to claim 16 including the steps of applying and maintaining longitudinal tension to said loose suture ends subsequent to throw placement and during the cutting operation.

* * * * *

UNITED STATES PATENT AND TRADEMARK OFFICE
CERTIFICATE OF CORRECTION

PATENT NO. : 5,133,723
DATED : July 28, 1992
INVENTOR(S) : Li et al.

It is certified that error appears in the above-identified patent and that said Letters Patent is hereby corrected as shown below:

Claim 1, column 21, line 57, the word "an" should be -- and --.

Signed and Sealed this

Twenty-first Day of September, 1993

*Attest:*

BRUCE LEHMAN

*Attesting Officer*         *Commissioner of Patents and Trademarks*